(12) United States Patent
Longo

(10) Patent No.: US 10,604,778 B2
(45) Date of Patent: Mar. 31, 2020

(54) BRCA2 MEDIATED PROTEIN PURIFICATION RECOMBINASE

(71) Applicant: Michael Longo, Whittier, CA (US)

(72) Inventor: Michael Longo, Whittier, CA (US)

(73) Assignee: IDEA SEED, LLC, City of Industry, CA (US)

( * ) Notice: Subject to any disclaimer, the term of this patent is extended or adjusted under 35 U.S.C. 154(b) by 0 days.

(21) Appl. No.: 15/555,966

(22) PCT Filed: Mar. 7, 2016

(86) PCT No.: PCT/US2016/021282
§ 371 (c)(1),
(2) Date: Sep. 5, 2017

(87) PCT Pub. No.: WO2016/141390
PCT Pub. Date: Sep. 9, 2016

(65) Prior Publication Data
US 2018/0037922 A1    Feb. 8, 2018

Related U.S. Application Data

(60) Provisional application No. 62/128,512, filed on Mar. 5, 2015.

(51) Int. Cl.
*C12P 21/02* (2006.01)
*C12N 15/62* (2006.01)
*C12N 9/12* (2006.01)
*C07K 14/47* (2006.01)

(52) U.S. Cl.
CPC .......... *C12P 21/02* (2013.01); *C07K 14/4703* (2013.01); *C12N 9/1241* (2013.01); *C12N 15/62* (2013.01); *C07K 2319/00* (2013.01); *C07K 2319/21* (2013.01); *C07K 2319/24* (2013.01)

(58) Field of Classification Search
None
See application file for complete search history.

(56) References Cited

U.S. PATENT DOCUMENTS

| 2006/0234293 A1* | 10/2006 | Venkitaraman | ........ C07K 14/47 435/7.1 |
| 2008/0280327 A1* | 11/2008 | Larsen | ................. C07K 14/005 435/69.7 |
| 2013/0203116 A1* | 8/2013 | Kowalczykowski | .. C12N 15/62 435/69.7 |

OTHER PUBLICATIONS

Chica et al. Curr Opin Biotechnol. Aug. 2005;16(4):378-84. (Year: 2005).*
Singh et al. Curr Protein Pept Sci. 2017, 18, 1-11 (Year: 2017).*
Accession Q06609. Jun. 1, 1994 (Year: 1994).*
Michelle E. Kimple et al., "Overview of Affinity Tags for Protein Purification." Current protocols in protein science vol. 73 Unit 9.9 (2013): 1-26.
Thorslud et al., "BRCA: an universal recombinase regulator." Oncogene vol. 26 (2007): 7720-30, 7723.
Zhenguo Lin et al., "Origins and evolution of the recA/RAD51 gene family: Evidence for ancient gene duplication and edosymbiotic gene transfer." PNAS vol. 103(27) (2006): 10328-10333, 10328.
Jaewon Min et al., "Identification of Rad51 regulation by BRCA2 using Caenorhabditis elegans BRCA2 and bimolecular fluorescence complementation analysis" (2007).

* cited by examiner

*Primary Examiner* — Christian L Fronda
(74) *Attorney, Agent, or Firm* — Marvin H. Kleinberg; Kleinberg & Lerner, LLP

(57) ABSTRACT

The invention is the products and methods associated with purifying overexpressed recombinant recombinases from a host cell line resulting in an un-tagged protein of interest without any additional, non-native amino acids. The invention employs at least one DNA vector that co-expresses a tagged fusion protein and the recombinase protein with the recombinase protein having an affinity for binding to the the tagged fusion protein. Isolation methods of the recombinase protein include the targeting of the tagged fusion protein.

10 Claims, 16 Drawing Sheets

Specification includes a Sequence Listing.

Heparin Resin Elution Profile

SEQUENCE LISTING

```
<160> NUMBER OF SEQ ID NOS: 24

<210> SEQ ID NO 1
<211> LENGTH: 32
<212> TYPE: DNA
<213> ORGANISM: Artificial Sequence
<220> FEATURE:
<223> OTHER INFORMATION: Primer

<400> SEQUENCE: 1
atatatacat atggcaatgc agatgcagct tg                                 32

<210> SEQ ID NO 2
<211> LENGTH: 38
<212> TYPE: DNA
<213> ORGANISM: Artificial Sequence
<220> FEATURE:
<223> OTHER INFORMATION: Primer

<400> SEQUENCE: 2
tatatcctag gttattagtc tttggcatct cccactcc                           38

<210> SEQ ID NO 3
<211> LENGTH: 32
<212> TYPE: DNA
<213> ORGANISM: Artificial Sequence
<220> FEATURE:
<223> OTHER INFORMATION: Primer

<400> SEQUENCE: 3
agttgcccat atgaaggagg atcaagttgt gg                                 32

<210> SEQ ID NO 4
<211> LENGTH: 39
<212> TYPE: DNA
<213> ORGANISM: Artificial Sequence
<220> FEATURE:
<223> OTHER INFORMATION: Primer

<400> SEQUENCE: 4
gtacaaccta ggttattact ccttcgcatc cccaattcc                          39

<210> SEQ ID NO 5
<211> LENGTH: 56
<212> TYPE: DNA
<213> ORGANISM: Artificial Sequence
<220> FEATURE:
<223> OTHER INFORMATION: Primer

<400> SEQUENCE: 5
attgggcgcg cctggaaaac ctgtattttc agggatccaa agaaccgacc ctgctg       56

<210> SEQ ID NO 6
<211> LENGTH: 36
<212> TYPE: DNA
```

```
<213> ORGANISM: Artificial Sequence
<220> FEATURE:
<223> OTHER INFORMATION: Primer

<400> SEQUENCE: 6
agctgcggcc gcttattagt cgaacaggtt tttaac                                   36

<210> SEQ ID NO 7
<211> LENGTH: 53
<212> TYPE: DNA
<213> ORGANISM: Artificial Sequence
<220> FEATURE:
<223> OTHER INFORMATION: Primer

<400> SEQUENCE: 7
actgcaactg aattccacca acgtcgctca gagatcatac agattactac tgg               53

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
agctgcggcc gcttatcagt ctttggcatc tcccactcc                               39

<210> SEQ ID NO 9
<211> LENGTH: 29
<212> TYPE: DNA
<213> ORGANISM: Artificial Sequence
<220> FEATURE:
<223> OTHER INFORMATION: Primer

<400> SEQUENCE: 9
gaataggatc caaagaaccg accctgctg                                          29

<210> SEQ ID NO 10
<211> LENGTH: 70
<212> TYPE: DNA
<213> ORGANISM: Artificial Sequence
<220> FEATURE:
<223> OTHER INFORMATION: Primer

<400> SEQUENCE: 10
ggaattcagt tgcagtggta aagccagagc cagtgctgcc agtgctgcca gtgtcgaaca        60 ggttttttaac                                                              70

<210> SEQ ID NO 11
<211> LENGTH: 39
<212> TYPE: DNA
<213> ORGANISM: Artificial Sequence
<220> FEATURE:
<223> OTHER INFORMATION: Primer

<400> SEQUENCE: 11
agctgcggcc gcttatcagt ctttggcatc tcccactcc                               39

<210> SEQ ID NO 12
<211> LENGTH: 1017
<212> TYPE: DNA
<213> ORGANISM: Homo sapiens

<400> SEQUENCE: 12
atggcaatgc agatgcagct tgaagcaaat gcagatactt cagtggaaga agaaagcttt        60
```

```
ggcccacaac ccatttcacg gttagagcag tgtggcataa atgccaacga tgtgaagaaa    120
ttggaagaag ctggattcca tactgtggag gctgttgcct atgcgccaaa gaaggagcta    180
ataaatatta agggaattag tgaagccaaa gctgataaaa ttctggctga ggcagctaaa    240
ttagttccaa tgggtttcac cactgcaact gaattccacc aaaggcggtc agagatcata    300
cagattacta ctggctccaa agagcttgac aaactacttc aaggtggaat tgagactgga    360
tctatcacag aaatgtttgg agaattccga actgggaaga cccagatctg tcatacgcta    420
gctgtcacct gccagcttcc cattgaccgg ggtggaggtg aaggaaaggc catgtacatt    480
gacactgagg gtacctttag gccagaacgg ctgctggcag tggctgagag gtatggtctc    540
tctggcagtg atgtcctgga taatgtagcc tatgctcgcg cgttcaacac agaccaccag    600
acccagctcc tttatcaagc atcagccatg atggtagaat ctaggtatgc actgcttatt    660
gtagacagtg ccaccgccct ttacagaaca gactactcgg tcgaggtgag ctttcagcc    720 aggcagatgc acttggccag gtttctgcgg atgcttctgc gactcgctga tgagtttggt    780
gtagcagtgg taatcactaa tcaggtggta gctcaagtgg atggagcagc gatgtttgct    840
gctgatccca aaaacctat tggaggaaat atcatcgccc atgcatcaac aaccagattg    900
tatctgagga aaggaagagg ggaaaccaga atctgcaaaa tctacgactc tccctgtctt    960
cctgaagctg aagctatgtt cgccattaat gcagatggag tgggagatgc caaagac     1017

<210> SEQ ID NO 13
<211> LENGTH: 93
<212> TYPE: DNA
<213> ORGANISM: Homo sapiens

<400> SEQUENCE: 13
aaagaaccga ccctgctggg tttccacacc gcttccggta aaaagttaa aatcgctaaa     60 gaatccctgg acaaagttaa aaacctgttc gac                                 93

<210> SEQ ID NO 14
<211> LENGTH: 765
<212> TYPE: DNA
<213> ORGANISM: Artificial Sequence
<220> FEATURE:
<223> OTHER INFORMATION: Fusion sequence

<400> SEQUENCE: 14
ggtttcacca ctgcaactga attccaccaa aggcggtcag agatcataca gattactact     60
ggctccaaag agcttgacaa actacttcaa ggtggaattg agactggatc tatcacagaa    120
atgtttggag aattccgaac tgggaagacc cagatctgtc atacgctagc tgtcacctgc    180
cagcttccca ttgaccgggg tggaggtgaa ggaaaggcca tgtacattga cactgagggt    240
acctttaggc cagaacggct gctggcagtg gctgagaggt atggtctctc tggcagtgat    300
gtcctggata tgtagccta tgctcgcgcg ttcaacacag accaccagac ccagctcctt    360
tatcaagcat cagccatgat ggtagaatct aggtatgcac tgcttattgt agacagtgcc    420
accgcccttt acagaacaga ctactcgggt cgaggtgagc tttcagccag gcagatgcac    480
ttggccaggt ttctgcggat gcttctgcga ctcgctgatg agtttggtgt agcagtggta    540
atcactaatc aggtggtagc tcaagtggat ggagcagcga tgtttgctgc tgatcccaaa    600
aaacctattg gaggaaatat catcgcccat gcatcaacaa ccagattgta tctgaggaaa    660
ggaagagggg aaaccagaat ctgcaaaatc tacgactctc cctgtcttcc tgaagctgaa    720
```

```
gctatgttcg ccattaatgc agatggagtg ggagatgcca aagac            765
```

<210> SEQ ID NO 15
<211> LENGTH: 1020
<212> TYPE: DNA
<213> ORGANISM: Homo sapiens

<400> SEQUENCE: 15

```
atgaaggagg atcaagttgt ggcggaagaa ccaggattcc aagatgaaga ggaatctttg     60
tttcaagata ttgacctgtt acagaaacat ggaattaacg tggctgacat taagaaactg    120
aaatcagtag gaatctgtac catcaaaggt atacagatga caacaagaag agctctatgc    180
aatgtcaaag gactctcaga agccaaagta gacaagatta agaggcagc gaacaaacta    240
attgaaccag gattcttgac tgcatttgag tatagtgaaa agaggaaaat ggttttccat    300
atcaccaccg ggagccagga atttgataag ttactaggag gtggaattga agtatggca    360
attacagaag cttttggaga atttcgtact ggaaaaaccc agctttctca taccctctgt    420
gtgacagctc aacttccagg agctggtggc tacccaggag aaagattat cttcattgat    480
acagaaaata ctttccgtcc agatcgcctt agggacattg ctgatcgctt aatgtagac    540
catgatgcag tactggacaa cgtactttat gcacgtgcat atactagtga acatcagatg    600
gagctacttg attatgtagc agcaaagttc catgaagaag ctggcatctt caagctattg    660
attatcgatt caataatggc acttttcga gtggatttca gtggccgtgg ggagttggcc    720
gaacggcagc aaaaattggc ccagatgttg tcacgactcc aaaaaatctc agaagaatat    780
aacgtggctg ttttttgtgac caatcaaatg actgccgatc aggagcaac tatgaccttt    840
caggcagatc ccaaaaaacc cattggggga cacattctgg ctcatgcttc aacaacaaga    900
ataagcttgc gaaagggaag aggagagctc agaattgcca gatttatga cagtcctgag    960
atgcctgaaa atgaagccac cttcgcaata actgctggag gaattgggga tgcgaaggag  1020
```

<210> SEQ ID NO 16
<211> LENGTH: 1296
<212> TYPE: DNA
<213> ORGANISM: Artificial Sequence
<220> FEATURE:
<223> OTHER INFORMATION: Fusion sequence

<400> SEQUENCE: 16

```
atggacacca ttcatcacca tcaccatcac aacactagta tgaaaatcga agaaggtaaa     60
ctggtaatct ggattaacgg cgataaaggc tataacggtc tcgctgaagt cggtaagaaa    120
ttcgagaaag ataccggaat taaagtcacc gttgagcatc cggataaact ggaagagaaa    180
ttcccacagg ttgcggcaac tggcgatggc cctgacatta tcttctgggc acacgaccgc    240
tttggtggct acgctcaatc tggcctgttg gctgaaatca ccccggacaa agcgttccag    300
gacaagctgt atccgtttac ctgggatgcc gtacgttaca acggcaagct gattgcttac    360
ccgatcgctg ttgaagcgtt atcgctgatt tataacaaag atctgctgcc gaacccgcca    420
aaaacctggg aagagatccc ggcgctggat aaagaactga agcgaaagg taagagcgcg    480
ctgatgttca acctgcaaga accgtacttc acctggccgc tgattgctgc tgacgggggt    540
tatgcgttca agtatgaaaa cggcaagtac gacattaaag acgtgggcgt ggataacgct    600
ggcgcgaaag cgggtctgac cttcctggtt gacctgatta aaaacaaaca catgaatgca    660
gacaccgatt actccatcgc agaagctgcc tttaataaag cgaaacagc gatgaccatc    720
aacggcccgt gggcatggtc caacatcgac accagcaaag tgaattatgg tgtaacggta    780
```

```
ctgccgacct tcaagggtca accatccaaa ccgttcgttg gcgtgctgag cgcaggtatt      840
gacgccgcca gtccgaacaa agagctggca aaagagttcc tcgaaaacta tctgctgact      900
gatgaaggtc tggaagcggt taataaagac aaaccgctgg gtgccgtagc gctgaagtct      960
tacgaggaag agttggcgaa agatccacgt attgccgcca caatggaaaa cgcccagaaa     1020
ggtgaaatca tgccgaacat cccgcagatg tccgcttttct ggtatgccgt gcgtactgcg     1080
gtgatcaacg ccgccagcgg tcgtcagact gtcgatgaag ccctgaaaga cgcgcagact     1140
aattcgagct cgactagtgg atctggtggg gcgcgcctgg aaaacctgta ttttcaggga     1200
tccaaagaac cgaccctgct gggttttcca ccgcttccg gtaaaaaagt taaaatcgct     1260
aaagaatccc tggacaaagt taaaaacctg ttcgac                               1296

<210> SEQ ID NO 17
<211> LENGTH: 2088
<212> TYPE: DNA
<213> ORGANISM: Artificial Sequence
<220> FEATURE:
<223> OTHER INFORMATION: Fusion sequence

<400> SEQUENCE: 17
atggacacca ttcatcacca tcaccatcac aacactagta tgaaaatcga agaaggtaaa       60
ctggtaatct ggattaacgg cgataaaggc tataacggtc tcgctgaagt cggtaagaaa      120
ttcgagaaag ataccggaat taaagtcacc gttgagcatc cggataaact ggaagagaaa      180
ttcccacagg ttgcggcaac tggcgatggc cctgacatta tcttctgggc acacgaccgc      240
tttggtggct acgctcaatc tggcctgttg gctgaaatca ccccggacaa agcgttccag      300
gacaagctgt atccgtttac ctgggatgcc gtacgttaca acggcaagct gattgcttac      360
ccgatcgctg ttgaagcgtt atcgctgatt tataacaaag atctgctgcc gaacccgcca      420
aaaacctggg aagagatccc ggcgctggat aaagaactga agcgaaagg taagagcgcg      480 ctgatgttca acctgcaaga accgtacttc acctggccgc tgattgctgc tgacggggt      540 tatgcgttca gtatgaaaaa cggcaagtac gacattaaag acgtgggcgt ggataacgct      600
ggcgcgaaag cgggtctgac cttcctggtt gacctgatta aaaacaaaca catgaatgca      660
gacaccgatt actccatcgc agaagctgcc tttaataaag gcgaaacagc gatgaccatc      720
aacggcccgt gggcatggtc caacatcgac accagcaaag tgaattatgg tgtaacggta      780
ctgccgacct tcaagggtca accatccaaa ccgttcgttg gcgtgctgag cgcaggtatt      840
gacgccgcca gtccgaacaa agagctggca aaagagttcc tcgaaaacta tctgctgact      900
gatgaaggtc tggaagcggt taataaagac aaaccgctgg gtgccgtagc gctgaagtct      960
tacgaggaag agttggcgaa agatccacgt attgccgcca caatggaaaa cgcccagaaa     1020
ggtgaaatca tgccgaacat cccgcagatg tccgcttttct ggtatgccgt gcgtactgcg     1080
gtgatcaacg ccgccagcgg tcgtcagact gtcgatgaag ccctgaaaga cgcgcagact     1140
aattcgagct cgactagtgg atctggtggg gcgcgcctgg aaaacctgta ttttcaggga     1200
tccaaagaac cgaccctgct gggttttcca ccgcttccg gtaaaaaagt taaaatcgct     1260
aaagaatccc tggacaaagt taaaaacctg ttcgacactg gcagcactgg cagcactggc     1320
tctggtttca ccactgcaac tgaattccac caaaggcggt cagagatcat acagattact     1380
actggctcca aagagcttga caaactactt caaggtggaa ttgagactgg atctatcaca     1440
gaaatgtttg gagaattccg aactgggaag acccagatct gtcatacgct agctgtcacc     1500
```

```
tgccagcttc ccattgaccg gggtggaggt gaaggaaagg ccatgtacat tgacactgag    1560
ggtaccttta ggccagaacg gctgctggca gtggctgaga ggtatggtct ctctggcagt    1620
gatgtcctgg ataatgtagc ctatgctcgc gcgttcaaca cagaccacca gacccagctc    1680
ctttatcaag catcagccat gatggtagaa tctaggtatg cactgcttat tgtagacagt    1740
gccaccgccc tttacagaac agactactcg ggtcgaggtg agctttcagc caggcagatg    1800
cacttggcca ggtttctgcg gatgcttctg cgactcgctg atgagtttgg tgtagcagtg    1860
gtaatcacta atcaggtggt agctcaagtg gatggagcag cgatgtttgc tgctgatccc    1920
aaaaaaccta ttggaggaaa tatcatcgcc catgcatcaa caaccagatt gtatctgagg    1980
aaaggaagag gggaaaccag aatctgcaaa atctacgact ctccctgtct tcctgaagct    2040
gaagctatgt tcgccattaa tgcagatgga gtgggagatg ccaaagac                 2088
```

<210> SEQ ID NO 18
<211> LENGTH: 339
<212> TYPE: PRT
<213> ORGANISM: Homo sapiens

<400> SEQUENCE: 18

```
Met Ala Met Gln Met Gln Leu Glu Ala Asn Ala Asp Thr Ser Val Glu
1               5                   10                  15

Glu Glu Ser Phe Gly Pro Gln Pro Ile Ser Arg Leu Glu Gln Cys Gly
                20                  25                  30

Ile Asn Ala Asn Asp Val Lys Lys Leu Glu Glu Ala Gly Phe His Thr
            35                  40                  45

Val Glu Ala Val Ala Tyr Ala Pro Lys Lys Glu Leu Ile Asn Ile Lys
        50                  55                  60

Gly Ile Ser Glu Ala Lys Ala Asp Lys Ile Leu Ala Glu Ala Ala Lys
65                  70                  75                  80

Leu Val Pro Met Gly Phe Thr Thr Ala Thr Glu Phe His Gln Arg Arg
                85                  90                  95

Ser Glu Ile Ile Gln Ile Thr Thr Gly Ser Lys Glu Leu Asp Lys Leu
                100                 105                 110

Leu Gln Gly Gly Ile Glu Thr Gly Ser Ile Thr Glu Met Phe Gly Glu
            115                 120                 125

Phe Arg Thr Gly Lys Thr Gln Ile Cys His Thr Leu Ala Val Thr Cys
130                 135                 140

Gln Leu Pro Ile Asp Arg Gly Gly Gly Glu Gly Lys Ala Met Tyr Ile
145                 150                 155                 160

Asp Thr Glu Gly Thr Phe Arg Pro Glu Arg Leu Leu Ala Val Ala Glu
                165                 170                 175

Arg Tyr Gly Leu Ser Gly Ser Asp Val Leu Asp Asn Val Ala Tyr Ala
            180                 185                 190

Arg Ala Phe Asn Thr Asp His Gln Thr Gln Leu Leu Tyr Gln Ala Ser
        195                 200                 205

Ala Met Met Val Glu Ser Arg Tyr Ala Leu Leu Ile Val Asp Ser Ala
    210                 215                 220

Thr Ala Leu Tyr Arg Thr Asp Tyr Ser Gly Arg Gly Glu Leu Ser Ala
225                 230                 235                 240

Arg Gln Met His Leu Ala Arg Phe Leu Arg Met Leu Leu Arg Leu Ala
                245                 250                 255

Asp Glu Phe Gly Val Ala Val Ile Thr Asn Gln Val Val Ala Gln
                260                 265                 270
```

```
Val Asp Gly Ala Ala Met Phe Ala Asp Pro Lys Lys Pro Ile Gly
            275                 280                 285

Gly Asn Ile Ile Ala His Ala Ser Thr Thr Arg Leu Tyr Leu Arg Lys
    290                 295                 300

Gly Arg Gly Glu Thr Arg Ile Cys Lys Ile Tyr Asp Ser Pro Cys Leu
305                 310                 315                 320

Pro Glu Ala Glu Ala Met Phe Ala Ile Asn Ala Asp Gly Val Gly Asp
                325                 330                 335

Ala Lys Asp

<210> SEQ ID NO 19
<211> LENGTH: 31
<212> TYPE: PRT
<213> ORGANISM: Homo sapiens

<400> SEQUENCE: 19

Lys Glu Pro Thr Leu Leu Gly Phe His Thr Ala Ser Gly Lys Lys Val
1               5                   10                  15

Lys Ile Ala Lys Glu Ser Leu Asp Lys Val Lys Asn Leu Phe Asp
            20                  25                  30

<210> SEQ ID NO 20
<211> LENGTH: 255
<212> TYPE: PRT
<213> ORGANISM: Artificial Sequence
<220> FEATURE:
<223> OTHER INFORMATION: Fusion Protein

<400> SEQUENCE: 20

Gly Phe Thr Thr Ala Thr Glu Phe His Gln Arg Arg Ser Glu Ile Ile
1               5                   10                  15

Gln Ile Thr Thr Gly Ser Lys Glu Leu Asp Lys Leu Leu Gln Gly Gly
            20                  25                  30

Ile Glu Thr Gly Ser Ile Thr Glu Met Phe Gly Glu Phe Arg Thr Gly
        35                  40                  45

Lys Thr Gln Ile Cys His Thr Leu Ala Val Thr Cys Gln Leu Pro Ile
    50                  55                  60

Asp Arg Gly Gly Gly Glu Gly Lys Ala Met Tyr Ile Asp Thr Glu Gly
65                  70                  75                  80

Thr Phe Arg Pro Glu Arg Leu Leu Ala Val Ala Glu Arg Tyr Gly Leu
                85                  90                  95

Ser Gly Ser Asp Val Leu Asp Asn Val Ala Tyr Ala Arg Ala Phe Asn
            100                 105                 110

Thr Asp His Gln Thr Gln Leu Leu Tyr Gln Ala Ser Ala Met Met Val
        115                 120                 125

Glu Ser Arg Tyr Ala Leu Leu Ile Val Asp Ser Ala Thr Ala Leu Tyr
    130                 135                 140

Arg Thr Asp Tyr Ser Gly Arg Gly Glu Leu Ser Ala Arg Gln Met His
145                 150                 155                 160

Leu Ala Arg Phe Leu Arg Met Leu Leu Arg Leu Ala Asp Glu Phe Gly
                165                 170                 175

Val Ala Val Val Ile Thr Asn Gln Val Val Ala Gln Val Asp Gly Ala
            180                 185                 190

Ala Met Phe Ala Ala Asp Pro Lys Lys Pro Ile Gly Gly Asn Ile Ile
        195                 200                 205

Ala His Ala Ser Thr Thr Arg Leu Tyr Leu Arg Lys Gly Arg Gly Glu
    210                 215                 220
```

```
Thr Arg Ile Cys Lys Ile Tyr Asp Ser Pro Cys Leu Pro Glu Ala Glu
225                 230                 235                 240

Ala Met Phe Ala Ile Asn Ala Asp Gly Val Gly Asp Ala Lys Asp
                245                 250                 255

<210> SEQ ID NO 21
<211> LENGTH: 340
<212> TYPE: PRT
<213> ORGANISM: Homo sapiens

<400> SEQUENCE: 21

Met Lys Glu Asp Gln Val Val Ala Glu Pro Gly Phe Gln Asp Glu
1               5                   10                  15

Glu Glu Ser Leu Phe Gln Asp Ile Asp Leu Leu Gln Lys His Gly Ile
                20                  25                  30

Asn Val Ala Asp Ile Lys Lys Leu Lys Ser Val Gly Ile Cys Thr Ile
                35                  40                  45

Lys Gly Ile Gln Met Thr Thr Arg Arg Ala Leu Cys Asn Val Lys Gly
50                  55                  60

Leu Ser Glu Ala Lys Val Asp Lys Ile Lys Glu Ala Ala Asn Lys Leu
65                  70                  75                  80

Ile Glu Pro Gly Phe Leu Thr Ala Phe Glu Tyr Ser Glu Lys Arg Lys
                85                  90                  95

Met Val Phe His Ile Thr Thr Gly Ser Gln Glu Phe Asp Lys Leu Leu
                100                 105                 110

Gly Gly Gly Ile Glu Ser Met Ala Ile Thr Glu Ala Phe Gly Glu Phe
                115                 120                 125

Arg Thr Gly Lys Thr Gln Leu Ser His Thr Leu Cys Val Thr Ala Gln
130                 135                 140

Leu Pro Gly Ala Gly Gly Tyr Pro Gly Gly Lys Ile Ile Phe Ile Asp
145                 150                 155                 160

Thr Glu Asn Thr Phe Arg Pro Asp Arg Leu Arg Asp Ile Ala Asp Arg
                165                 170                 175

Phe Asn Val Asp His Asp Ala Val Leu Asp Asn Val Leu Tyr Ala Arg
                180                 185                 190

Ala Tyr Thr Ser Glu His Gln Met Glu Leu Leu Asp Tyr Val Ala Ala
                195                 200                 205

Lys Phe His Glu Glu Ala Gly Ile Phe Lys Leu Leu Ile Ile Asp Ser
210                 215                 220

Ile Met Ala Leu Phe Arg Val Asp Phe Ser Gly Arg Gly Glu Leu Ala
225                 230                 235                 240

Glu Arg Gln Gln Lys Leu Ala Gln Met Leu Ser Arg Leu Gln Lys Ile
                245                 250                 255

Ser Glu Glu Tyr Asn Val Ala Val Phe Val Thr Asn Gln Met Thr Ala
                260                 265                 270

Asp Pro Gly Ala Thr Met Thr Phe Gln Ala Asp Pro Lys Lys Pro Ile
                275                 280                 285

Gly Gly His Ile Leu Ala His Ala Ser Thr Thr Arg Ile Ser Leu Arg
                290                 295                 300

Lys Gly Arg Gly Glu Leu Arg Ile Ala Lys Ile Tyr Asp Ser Pro Glu
305                 310                 315                 320

Met Pro Glu Asn Glu Ala Thr Phe Ala Ile Thr Ala Gly Gly Ile Gly
                325                 330                 335

Asp Ala Lys Glu
```

<210> SEQ ID NO 22
<211> LENGTH: 432
<212> TYPE: PRT
<213> ORGANISM: Artificial Sequence
<220> FEATURE:
<223> OTHER INFORMATION: Fusion protein

<400> SEQUENCE: 22

```
Met Asp Thr Ile His His His His His His Asn Thr Ser Met Lys Ile
1               5                   10                  15

Glu Glu Gly Lys Leu Val Ile Trp Ile Asn Gly Asp Lys Gly Tyr Asn
            20                  25                  30

Gly Leu Ala Glu Val Gly Lys Lys Phe Glu Lys Asp Thr Gly Ile Lys
        35                  40                  45

Val Thr Val Glu His Pro Asp Lys Leu Glu Glu Lys Phe Pro Gln Val
    50                  55                  60

Ala Ala Thr Gly Asp Gly Pro Asp Ile Ile Phe Trp Ala His Asp Arg
65                  70                  75                  80

Phe Gly Gly Tyr Ala Gln Ser Gly Leu Leu Ala Glu Ile Thr Pro Asp
                85                  90                  95

Lys Ala Phe Gln Asp Lys Leu Tyr Pro Phe Thr Trp Asp Ala Val Arg
            100                 105                 110

Tyr Asn Gly Lys Leu Ile Ala Tyr Pro Ile Ala Val Glu Ala Leu Ser
        115                 120                 125

Leu Ile Tyr Asn Lys Asp Leu Leu Pro Asn Pro Pro Lys Thr Trp Glu
130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
            180                 185                 190

Lys Asp Val Gly Val Asp Asn Ala Gly Ala Lys Ala Gly Leu Thr Phe
        195                 200                 205

Leu Val Asp Leu Ile Lys Asn Lys His Met Asn Ala Asp Thr Asp Tyr
210                 215                 220

Ser Ile Ala Glu Ala Ala Phe Asn Lys Gly Glu Thr Ala Met Thr Ile
225                 230                 235                 240

Asn Gly Pro Trp Ala Trp Ser Asn Ile Asp Thr Ser Lys Val Asn Tyr
                245                 250                 255

Gly Val Thr Val Leu Pro Thr Phe Lys Gly Gln Pro Ser Lys Pro Phe
            260                 265                 270

Val Gly Val Leu Ser Ala Gly Ile Asp Ala Ala Ser Pro Asn Lys Glu
        275                 280                 285

Leu Ala Lys Glu Phe Leu Glu Asn Tyr Leu Leu Thr Asp Glu Gly Leu
290                 295                 300

Glu Ala Val Asn Lys Asp Lys Pro Leu Gly Ala Val Ala Leu Lys Ser
305                 310                 315                 320

Tyr Glu Glu Glu Leu Ala Lys Asp Pro Arg Ile Ala Ala Thr Met Glu
                325                 330                 335

Asn Ala Gln Lys Gly Glu Ile Met Pro Asn Ile Pro Gln Met Ser Ala
            340                 345                 350

Phe Trp Tyr Ala Val Arg Thr Ala Val Ile Asn Ala Ala Ser Gly Arg
```

```
                355                 360                 365
Gln Thr Val Asp Glu Ala Leu Lys Asp Ala Gln Thr Asn Ser Ser Ser
370                 375                 380

Thr Ser Gly Ser Gly Gly Ala Arg Leu Glu Asn Leu Tyr Phe Gln Gly
385                 390                 395                 400

Ser Lys Glu Pro Thr Leu Leu Gly Phe His Thr Ala Ser Gly Lys Lys
                405                 410                 415

Val Lys Ile Ala Lys Glu Ser Leu Asp Lys Val Lys Asn Leu Phe Asp
                420                 425                 430

<210> SEQ ID NO 23
<211> LENGTH: 696
<212> TYPE: PRT
<213> ORGANISM: Artificial Sequence
<220> FEATURE:
<223> OTHER INFORMATION: Fusion protein

<400> SEQUENCE: 23

Met Asp Thr Ile His His His His His Asn Thr Ser Met Lys Ile
1               5                   10                  15

Glu Glu Gly Lys Leu Val Ile Trp Ile Asn Gly Asp Lys Gly Tyr Asn
                20                  25                  30

Gly Leu Ala Glu Val Gly Lys Lys Phe Glu Lys Asp Thr Gly Ile Lys
            35                  40                  45

Val Thr Val Glu His Pro Asp Lys Leu Glu Glu Lys Phe Pro Gln Val
        50                  55                  60

Ala Ala Thr Gly Asp Gly Pro Asp Ile Ile Phe Trp Ala His Asp Arg
65                  70                  75                  80

Phe Gly Gly Tyr Ala Gln Ser Gly Leu Leu Ala Glu Ile Thr Pro Asp
                85                  90                  95

Lys Ala Phe Gln Asp Lys Leu Tyr Pro Phe Thr Trp Asp Ala Val Arg
            100                 105                 110

Tyr Asn Gly Lys Leu Ile Ala Tyr Pro Ile Ala Val Glu Ala Leu Ser
        115                 120                 125

Leu Ile Tyr Asn Lys Asp Leu Leu Pro Asn Pro Pro Lys Thr Trp Glu
130                 135                 140

Glu Ile Pro Ala Leu Asp Lys Glu Leu Lys Ala Lys Gly Lys Ser Ala
145                 150                 155                 160

Leu Met Phe Asn Leu Gln Glu Pro Tyr Phe Thr Trp Pro Leu Ile Ala
                165                 170                 175

Ala Asp Gly Gly Tyr Ala Phe Lys Tyr Glu Asn Gly Lys Tyr Asp Ile
            180                 185                 190

Lys Asp Val Gly Val Asp Asn Ala Gly Ala Lys Ala Gly Leu Thr Phe
        195                 200                 205

Leu Val Asp Leu Ile Lys Asn Lys His Met Asn Ala Asp Thr Asp Tyr
210                 215                 220

Ser Ile Ala Glu Ala Ala Phe Asn Lys Gly Glu Thr Ala Met Thr Ile
225                 230                 235                 240

Asn Gly Pro Trp Ala Trp Ser Asn Ile Asp Thr Ser Lys Val Asn Tyr
                245                 250                 255

Gly Val Thr Val Leu Pro Thr Phe Lys Gly Gln Pro Ser Lys Pro Phe
            260                 265                 270

Val Gly Val Leu Ser Ala Gly Ile Asp Ala Ala Ser Pro Asn Lys Glu
        275                 280                 285

Leu Ala Lys Glu Phe Leu Glu Asn Tyr Leu Leu Thr Asp Glu Gly Leu
```

```
            290                 295                 300

Glu Ala Val Asn Lys Asp Lys Pro Leu Gly Ala Val Ala Leu Lys Ser
305                 310                 315                 320

Tyr Glu Glu Glu Leu Ala Lys Asp Pro Arg Ile Ala Ala Thr Met Glu
                325                 330                 335

Asn Ala Gln Lys Gly Glu Ile Met Pro Asn Ile Pro Gln Met Ser Ala
                340                 345                 350

Phe Trp Tyr Ala Val Arg Thr Ala Val Ile Asn Ala Ala Ser Gly Arg
                355                 360                 365

Gln Thr Val Asp Glu Ala Leu Lys Asp Ala Gln Thr Asn Ser Ser Ser
        370                 375                 380

Thr Ser Gly Ser Gly Gly Ala Arg Leu Glu Asn Leu Tyr Phe Gln Gly
385                 390                 395                 400

Ser Lys Glu Pro Thr Leu Leu Gly Phe His Thr Ala Ser Gly Lys Lys
                405                 410                 415

Val Lys Ile Ala Lys Glu Ser Leu Asp Lys Val Lys Asn Leu Phe Asp
                420                 425                 430

Thr Gly Ser Thr Gly Ser Thr Gly Ser Gly Phe Thr Thr Ala Thr Glu
        435                 440                 445

Phe His Gln Arg Arg Ser Glu Ile Ile Gln Ile Thr Thr Gly Ser Lys
        450                 455                 460

Glu Leu Asp Lys Leu Leu Gln Gly Gly Ile Glu Thr Gly Ser Ile Thr
465                 470                 475                 480

Glu Met Phe Gly Glu Phe Arg Thr Gly Lys Thr Gln Ile Cys His Thr
                485                 490                 495

Leu Ala Val Thr Cys Gln Leu Pro Ile Asp Arg Gly Gly Gly Glu Gly
                500                 505                 510

Lys Ala Met Tyr Ile Asp Thr Glu Gly Thr Phe Arg Pro Glu Arg Leu
                515                 520                 525

Leu Ala Val Ala Glu Arg Tyr Gly Leu Ser Gly Ser Asp Val Leu Asp
        530                 535                 540

Asn Val Ala Tyr Ala Arg Ala Phe Asn Thr Asp His Gln Thr Gln Leu
545                 550                 555                 560

Leu Tyr Gln Ala Ser Ala Met Met Val Glu Ser Arg Tyr Ala Leu Leu
                565                 570                 575

Ile Val Asp Ser Ala Thr Ala Leu Tyr Arg Thr Asp Tyr Ser Gly Arg
                580                 585                 590

Gly Glu Leu Ser Ala Arg Gln Met His Leu Ala Arg Phe Leu Arg Met
                595                 600                 605

Leu Leu Arg Leu Ala Asp Glu Phe Gly Val Ala Val Val Ile Thr Asn
        610                 615                 620

Gln Val Val Ala Gln Val Asp Gly Ala Ala Met Phe Ala Ala Asp Pro
625                 630                 635                 640

Lys Lys Pro Ile Gly Gly Asn Ile Ile Ala His Ala Ser Thr Thr Arg
                645                 650                 655

Leu Tyr Leu Arg Lys Gly Arg Gly Glu Thr Arg Ile Cys Lys Ile Tyr
                660                 665                 670

Asp Ser Pro Cys Leu Pro Glu Ala Glu Ala Met Phe Ala Ile Asn Ala
                675                 680                 685

Asp Gly Val Gly Asp Ala Lys Asp
        690                 695

<210> SEQ ID NO 24
```

<211> LENGTH: 597
<212> TYPE: DNA
<213> ORGANISM: Artificial Sequence
<220> FEATURE:
<223> OTHER INFORMATION: pRSFDuet-1 plasmid multiple cloning site

<400> SEQUENCE: 24

```
gccataccgc gaaaggtttt gcgccattcg atggtgtccg ggatctcgac gctctccctt      60
atgcgactcc tgcattagga aattaatacg actcactata ggggaattgt gagcggataa     120
caattcccct gtagaaataa ttttgtttaa ctttaataag gagatatacc atgggcagca     180
gccatcacca tcatcaccac agccaggatc cgaattcgag ctcggcgcgc ctgcaggtcg     240
acaagcttgc ggccgcataa tgcttaagtc gaacagaaag taatcgtatt gtacacggcc     300
gcataatcga aattaatacg actcactata ggggaattgt gagcggataa caattcccca     360
tcttagtata ttagttaagt ataagaagga gatatacata tggcagatct caattggata     420
tcggccggcc acgcgatcgc tgacgtcggt accctcgagt ctggtaaaga aaccgctgct     480
gcgaaatttg aacgccagca catggactcg tctactagcg cagcttaatt aacctaggct     540
gctgccaccg ctgagcaata actagcataa cccttgggg cctctaaacg ggtcttg        597
```

BRCA2 MEDIATED PROTEIN PURIFICATION RECOMBINASE

This application claims the benefit of U.S. Provisional Application No. 62/128,512 filed Mar. 5, 2015.

BACKGROUND OF THE INVENTION

1. Field of the Invention

The present invention relates to methods for isolation of recombinant proteins, and namely methods that involve the purification of recombinases.

2. General Background and State of the Art

Recombinases play a vital role in the life cycle of a cell. In Prokaryotes, the RecA recombinase is the molecular machine that facilitates repair of DNA double strand breaks (DSBs) via homologous recombination. In Eukaryotes, Rad51 and Dmc1 are the RecA homologs that mediate homologous recombination.

Both RAD51 and DMC1 proteins coded for by the Rad51 and Dmc1 genes, respectively, have a molecular weight of roughly 37 kilodaltons (kDa), have very similar amino acids sequences, and unsurprisingly are structural homologs as well. The common features of these recombinases are 1) a conserved globular ATPase domain joined by 2) an elbow-like linker region to a 3) pendulum-like bundle of helices in the N-terminus of the structure. The ATPase domain binds and hydrolyzes ATP through conserved Walker A and Walker B motifs, but also contains flexible loops, L1 and L2, which are responsible for the DNA binding capacity of the proteins. The role of the N-terminal domain is thought to also involve DNA interaction in some capacity.

Within the elbow-like linker region, which physically connects these two domains, is a conserved F-X-X-A motif, with F representing phenylalanine, X representing a non-conserved amino acid, and A representing alanine. It is through this F-X-X-A motif that these recombinases are able to polymerize into higher order multimeric structures. The larger hydrophobic residue, F, plugs into a deep hydrophobic pocket located in the globular ATPase domain of a neighboring molecule, while the A residue sits in an adjacent shallower pocket. This sort of head-to-tail arrangement facilitates the formation of large macromolecular structures, like the nucleoprotein filaments that both RAD51 and DMC1 have been shown to produce.

An important interaction of RAD51 is with the Breast Cancer Susceptibility Protein 2, BRCA2. BRCA2 interacts with RAD51 through 2 separate and distinct modes. One mode is characterized by the interaction of RAD51 with the BRC repeat region of BRCA2, which in humans consist of 8 BRC repeats termed BRC1-8. The BRC repeat binds mainly by mimicking RAD51 multimeric association. Thus the BRC repeat contains a conserved F-X-X-A motif and bind to the pockets of a RAD51 ATPase domain. In addition to the conserved F-X-X-A motif, BRC repeats make additional contacts with the RAD51 ATPase domain further stabilizing the interaction. In this mode of binding, one RAD51 molecule binds to one BRC repeat in a 1:1 ratio.

In the C-terminal region of BRCA2 is another motif that binds to RAD51, but through a different molecular approach, as it binds to a multimeric form of RAD51, as opposed to the 1:1 stoichiometry of the BRC interaction.

Upon the occurrence of a DSB, the broken DNA ends are resected by the Exo1/Dna2 nucleases to yield 3' single stranded overhangs. RAD51 monomers bind and polymerize along the length of the 3' overhangs, producing RAD51 nucleoprotein filaments. It is the RAD51 nucleoprotein filament that drives the subsequent search for homologous sequence.

This search for a homologous sequence is accomplished specifically by catalyzing the invasion of the 3' overhang strand into an intact double strand DNA molecule, typically a sister chromosome. This process is termed strand invasion. The invading 3' overhang can base pair with the homologous sequence and use the complementary sequence as a template to initiate repair synthesis.

The DMC1 recombinase performs the same role as RAD51, but in meiotic cells where DSBs are intentionally introduced during meiosis. The ensuing strand invasion is critical for the pairing of homologous chromosomes during prophase 1.

Standard established protocols for the purification of recombinant Rad51 and Dmc1 have typically involved a spermadine precipitation step as an initial means of isolating the target protein from soluble lysate, followed by subsequent resolubilizing and further chromatographic separation. The yields of such protocols are not abundant and as a consequence, frequent re-preparation is required.

Alternatively to the precipitation-based method, purification of RAD51/DMC1 has also been accomplished by fusing an affinity tag to either the amino-terminus or the carboxy-terminus of the target protein. Though such tags can be engineered to be proteolytically removed, such a process generally leaves additional residues not present in the native protein sequence. In addition, the requirement for a sequence-specific protease can be burdensome and incur additional cost.

INVENTION SUMMARY

The invention is the products and methods associated with purifying overexpressed recombinant RAD51 or DMC1 proteins by utilizing their natural protein-protein interactions to efficiently isolate and enrich them from the soluble lysate, then subsequently separate them from their cognate interaction partner in a later chromatographic step. The final product is the full length, un-tagged protein of interest without any additional, non-native amino acids.

Recombinant RAD51 or DMC1 protein expression can be done in any expression system of choice (i.e. bacteria, yeast, insect cell, or mammalian cell).

Possible bacterial strains that may be used for the cloning and expression of the recombinant vector may be, but not limited to D5α, BL21, BL21 (DE3), JM109, JM109 (DE3), HB101 or derivatives thereof. Possible plasmids for gene modification and protein expression in said bacteria may be any of the pET vectors as described in the Novagen pET System Manual (www.emdmillipore.com) or any pBAD expression vectors provided by Invitorgen Life Technologies (www.lifetechnologies.com). pQE vectors may also be used to create a recombinant vector. In another preferred embodiment, a pRSF-Duet 1 dual expression vector (Novagen) may also be used.

In the alternate, the RAD51 or DMC1 containing construct may also be expressed in a mammalian cell system. Possible plasmids for use in mammalian cellular expression systems may be a pcDNA expression vector under the control of a CMV promoter such as pcDNA3.1+ as provided by Life Technologies (www.lifetechnologies.com) or a high expression vector such pEF-BOS or a pEF-BOS derivative as described by Mizushima et. al. Nuc. Adi. Res. 18:17 (1990). Possible mammalian cell lines may be HEK293E suspension cells.

The recombinant RAD51 protein is co-overexpressed with a fusion protein wherein the fusion protein includes sequences for an affinity tag (such as MBP or GST), and the BRC4 F-X-X-A repeat motif of the Breast Cancer Susceptibility Protein (BRCA2). An additional tag such as a polyhistidine tag (hisTag) generally of six histidine residues may be added to the fusion protein to facilitate another affinity tag that may be utilized for recombinant protein purification. The sequence for the RAD51 protein can be the full-length, native sequence or a specific truncation of the native sequence, or a desired, specific mutation of the native sequence. If an MBP tag was used, the resulting fusion protein is a hisTag-MBP-BRC4 fusion protein. The hisTag may be on the N-terminus or C-terminus of the fusion protein. Other sequences may encode for tags such as, but not limited to, a MYC tag, FLAG tag, Strep tag, MBP tag, GST tag or any other protein tags known by one of ordinary skill in the art.

Since F-X-X-A interaction is largely a hydrophobic interaction, cells may be lysed using buffers that stabilize hydrophobic interactions. Such buffers may have a high salt concentration such as $(NH_4)_2SO_4$, $K_2PO_4$, sodium acetate, NaCl, or KCl) or a detergent (such as deoxycholate or Triton-X 100). Additional additives to the lysis buffer or in subsequent buffers used in the protein purification process may be glycerol, carbohydrates (such as glucose or sucrose), metal chelators (such as EDTA or EGTA), reducing agents (such as dithiothreitol, dithioerythritol, 2-mercaptoethanol, or tris(2-carboxyethyl)phosphine), ligands (such as ATP, ADP, AMP, or GTP), metal ions or cofactors (such as $Mg^{2+}$, $Ca^{2+}$, $Fe^{2+}$, $Fe^{3+}$, $Mn^{2+}$, $Zn^{2+}$, or $Cu^{2+}$), protease inhibitors (such as pepstatin, leupeptin, or phenylmethanesulfonyl fluoride), or any buffer additive known to one with ordinary skill in the art.

Once the cells co-expressing the RAD51 protein and the hisTag-MBP-BRC4 tagged protein are lysed and clarified, the soluble lysate may be applied to a resin specific to the MBP affinity tag that is part of the hisTag-MBP-BRC4 protein. The MBP tagged protein may be applied to a resin containing immobilized amylose. In an alternative embodiment, a GST tag may be used instead the MBP tag. A GST tag may require a resin containing immobilized glutathione. The RAD51 protein interacts with the F-X-X-A motif in the hisTag-MBP-BRC4 protein thus RAD51 will be bound with the hisTag-MBP-BRC4 protein to the immobilized resin. Following binding, and a subsequent wash step, the BRC4-containing tagged protein is eluted from the resin, for example eluted with maltose, which results in a significant enrichment in the eluate of the hisTag-MBP-BRC4 protein and the RAD51 protein which co-purifies with the hisTag-MBP-BRC4 protein.

Alternatively, once the cells co-expressing the RAD51 protein and the hisTag-MBP-BRC4 tagged protein are lysed and clarified, the soluble lysate may be applied to a resin specific to the 6×His tag that is part of the hisTag-MBP-BRC4 protein. For example, a resin containing ligands such as immobilized nitrile triacetic acid (NTA), iminodiacetic acid (IDA), or tris(carboxymethyl)ethylene diamine (TED) or a resin that binds divalent metal cations such as $Ni^{2+}$ or $Co^{2+}$ maybe used. The RAD51 protein interacts with the F-X-X-A motif in the hisTag-MBP-BRC4 protein, thus RAD51 will be bound with the hisTag-MBP-BRC4 protein to the immobilized resin. Following binding, and a subsequent wash step, the BRC4-containing tagged protein is eluted from the resin. For example, an imidazole wash results in a significant enrichment in the eluate of the hisTag-MBP-BRC4 protein and the RAD51 protein which co-purifies with the hisTag-MBP-BRC4 protein.

Separating the RAD51 protein from the bound hisTag-MBP-BRC4 protein may be accomplished by utilizing a ligand that provides inherent RAD51 binding, and little to no binding affinity for the hisTag-MBP-BRC4 fusion protein. One example is a resin containing an immobilized ligand that is known to generally mimic DNA molecules. One exemplary ligand is a heparin. Other ligands may be employed that are known to one with ordinary skill in the art with the properties that allow efficient binding to a variety of DNA binding proteins. Before applying the sample, a heparin containing phase requires a salt concentration that should be considered and diluted accordingly (50-100 mM NaCl optimally). By applying the BRC4-containing tagged fusion protein and RAD51 or DMC1 protein containing eluate to heparin, the BRC4-containing tagged fusion protein may remain in the unbound state and flow through the heparin containing phase, or weakly bind to heparin thereby eluting very early in the elution profile as the salt concentration gradually applied to the resin increases. As the salt concentration reaches a relatively high concentration, roughly 50-700 mM NaCl, RAD51 or DMC1 elutes from the heparin ligand, thereby successfully separating RAD51 or DMC1 from its BRC4-containing tagged fusion protein. Chromatography or other methods that involve the use a ligand bound solid support may be used in this isolation step.

The RAD51 protein that eluted from heparin resin may then be applied to a chromatography column filled with size exclusion chromatography (i.e. gel filtration) media in order to remove any remaining contaminants. Examples of a gel filtration resin may be Superdex (for example Superdex 200), Sephacryl (for example S-100 HR), Superose (for example Superose 6), Sephadex (for example Sephadex G-10), or Sepharose (for example Sepharose 4B) variety resins. This final gel filtration step may also serve to exchange the protein into a desired buffer or possibly concentrate the sample. As the RAD51 is generally in a large, multimeric form, it will elute mainly in the void volume of a standard gel filtration column.

In place of heparin, other ion exchange ligands such as a cation exchange or anion exchange can be successfully used to separate RAD51 from the hisTag-MBP-BRC4 protein as well as from other contaminant proteins. RAD51 may bind to an alternative ligand, though the inherit capacity of the chosen affinity tag for the particular ion-exchange resin would have to be taken into consideration.

Also, in place of the BRC4 motif, other BRC motifs, as well as the C-terminal RAD51 binding motif of BRCA2, may be used to initially isolate and/or enrich RAD51 from cell lysate.

For the purification of DMC1, the same principle described above may be employed in place of RAD51. However, not the isolation does not depend on BRC4 repeat as the subtle differences in protein sequence make DMC1 a poor binding partner for a BRC4 repeat.

Recombinant DMC1 protein expression can be done in any expression system of choice (i.e. bacteria, yeast, insect cell, or mammalian cell). The recombinant DMC1 protein is co-overexpressed with a fusion protein wherein the fusion protein includes sequences for an affinity tag (such as MBP or GST), and the BRC4 F-X-X-A repeat motif of the Breast Cancer Susceptibility Protein (BRCA2), and the RAD51 F-X-X-A motif, and an additional tag (such as a polyhistidine tag) may be utilized for recombinant protein purification. If an MBP tag is used in making the fusion protein construct, the resulting fusion protein is a hisTag-MBP-BRC4-RAD51 fusion protein. The sequence for the RAD51 protein may be the full-length, native sequence or a specific truncation of the native sequence, or a desired, specific mutation of the native sequence. The sequence for the co-overexpressed DMC1 protein can be the full-length, native sequence or a specific truncation of the native sequence, or a desired, specific mutation of the native sequence. In an alternate embodiment of the hisTag-MBP-BRC4-RAD51 fusion protein, BCR4 may be substituted by any of BRCA2 1-8 sequence. In yet another embodiment, the MBP sequence in hisTag-MBP-BRC4-RAD51 may be substituted for a different protein tag, for example at GST tag. The 6×His tag may be on the N-terminus or C-terminus of the fusion protein.

As in the exemplary RAD51 purification method described above, the hisTag-MBP-BCR4-RAD51 fusion protein containing the RAD51 F-X-X-A ATPase domain may be co-overexpressed with the DMC1 protein. To isolate DMC1 from cell lysate, the interaction between DMC1 and the RAD51 F-X-X-A ATPase domain can be exploited to enrich and subsequently purify DMC1. For example, the RAD51 F-X-X-A ATPase domain in the hisTag-MBP-BCR4-RAD51 fusion protein facilitates the interaction with additional DMC1 molecules. When the fusion protein hisTag-MBP-BCR4-RAD51 fusion protein is isolated from clarified lysate, DMC1 will be enriched along with it. Subsequently applying the eluate to a heparin as described for RAD51 will result in the hisTag-MBP-BCR4-RAD51 fusion protein being separated from DMC1.

To diminish the binding capacity of the F-X-X-A ATPase-fusion to heparin, the ATPase domain may be engineered to have its DNA binding loops (L1 and/or L2) removed. Thus, the DMC1 separation via heparin or an equivalent resin may be more efficient.

DETAILED DESCRIPTION OF THE INVENTION

(i) Definitions

Figure 1:
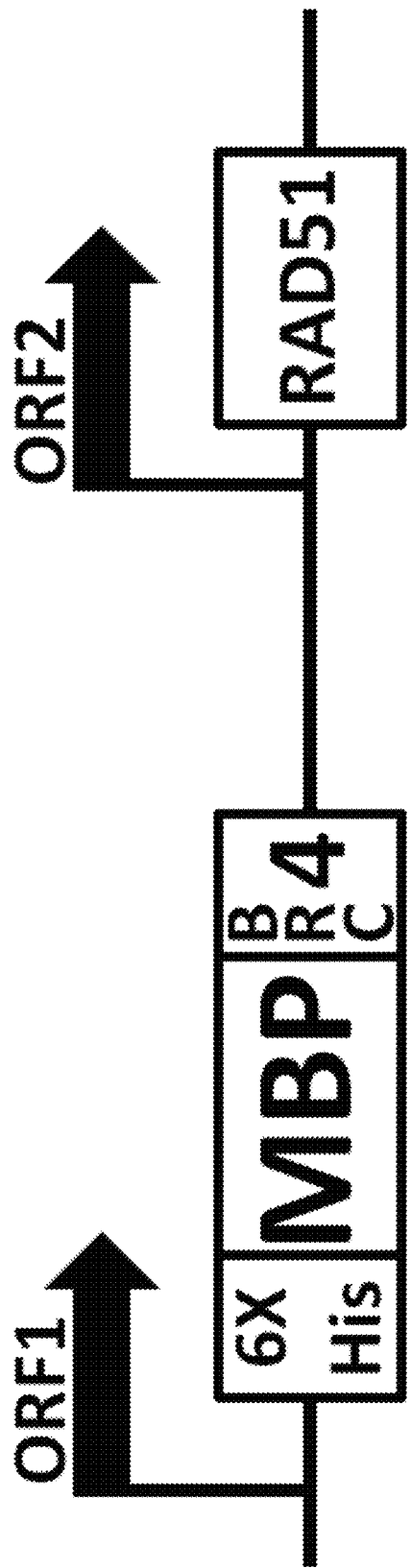
FIG. 1. Diagram representation of vector construct for co-overexpression of 6×his-MBP-tagged-BRC4 fusion protein from Open Reading Frame 1 (ORF1) and RAD51 protein from Open Reading Frame 2 (ORF 2).

The following definitions, unless otherwise stated, apply to all aspects and embodiments of the present application.

The present invention contemplates the co-expression and purification of a protein and recombinant protein.

An "oligonucleotide" refers to a single stranded DNA, RNA, or a DNA-RNA hybrid nucleic acid strand that may be approximately 18 to 30 nucleotides in length. Oligonucleotides can hybridize to genetic material such as DNA, cDNA, or mRNA. Oligonucleotides can be labeled at their 5'-terminus via an amino- or thiol-linker or at the 3'-terminus via an amino link with, but not limited to, fluorophores such as Cy3™, Cy5™, fluorescein, quenchers such as Dabcyl or T-Dabsyl, or alternative labels such as biotin and radioisotopes. Labeled oligonucleotides may function as probes to detect the presence of nucleic acids with a complementary nucleic acid sequence. Labeled or unlabeled oligonucleotides may also be used as primers necessary for performing PCR when cloning or detecting the presence of a gene. Oligonucleotides are prepared synthetically by solid-phase synthesis using modified or unmodified 2'-deoxynucleosides (dA, dC, dG, and dT) or ribonucleosides (A, C, G, U).

The terms "protein", "peptide", and "polypeptide" refer to a linear macromolecular polymer of at least two natural or non-natural amino acids covalently linked together by peptide bonds. A protein, peptide, or polypeptide has a free amino group at the N-terminus and a free carboxyl group at the C-terminus unless circular or specifically tagged at the N- or C-terminus. The amino acid sequence of a protein, peptide, or a polypeptide is determined by the nucleotide sequence of a gene. Proteins, peptides and polypeptides may have a primary, secondary, and tertiary structure. At times, the protein, peptide, or polypeptide may also be post-translationally modified with prosthetic groups or cofactors.

The term "gene" refers to a specific DNA sequence that can be transcribed into RNA which can then be translated into a peptide or a polypeptide. Regions in the DNA sequence of a gene may also include regulatory regions, the transcribed sequence for RNA, and the coding sequence with a start and stop codon that is translated into a protein. Transcriptional and translational regulatory regions that control the expression of a gene may include promoters, enhancers, terminators, and in the case of eukaryotic expression a polyadenylation signal.

The term "cloning vector" refers to pieces of nucleic acid that can be used for the insertion and stable preservation of foreign pieces of DNA within an organism. The cloning vector may be a plasmid, bacertiophage, cosmid, bacterial artificial chromosome, or a yeast artificial chromosome. Cloning vectors may be used for creating genomic libraries such as in the invention herein.

A "plasmid" is a vector that refers to an independently replicating circular double-stranded piece of DNA. The plasmid may contain an origin of replication such as the E. coli oriC, a selectable antibiotic resistance gene conferring resistance to but not limited to β-lactam, macrolide, and aminoglycosides antibiotics, a promoter sequence under expression control, and a multiple cloning site containing restriction sites which may or may not contain a coding sequence for an antibody like protein described herein.

The plasmid may be an "expression plasmid". Expression plasmids allow for the expression of a cloned gene. An expression plasmid contains an inducible promoter region that allows for the regulation and induction of gene expression of a gene cloned into the plasmid's multiple cloning site, a ribosomal binding site, a start codon, a stop codon, and a termination of transcription sequence.

The term "promoter sequence" is a region of DNA either upstream or downstream from the site of initiation of transcription of a gene. As used herein, a bacterial promoter includes necessary consensus sequences of TTGACA at the −35 and a Pribnow box TATAAT sequence at the −10 position upstream of the start of transcription, and may also contain an UP element upstream of the −35 region.

The term "recombinant protein" refers to a protein that is expressed from an engineered "recombinant DNA" coding sequence. Recombinant DNA combines at least two separate DNA strands into one strand that would not have been normally made in nature. Molecular cloning is used to construct recombinant DNA and may involve the amplification of a DNA fragment of interest and then inserting the fragment into a cloning vector. The recombinant DNA is then introduced into a host organism which is then screened and selected for the presence of the inserted recombinant DNA.

The term "amplification" refers to the act of mass replication of a genetic sequence. Amplification of a genetic sequence may be performed by polymerase chain reaction (PCR) using primers that hybridize to flanking ends of a genetic sequence of interest. Amplification of a genetic sequence may also be performed in vivo by transforming bacteria with a plasmid or transfecting a host cell with a virus that carries the recombinant genetic sequence of interest.

The term "protein expression" refers to the production of protein within a host cell such as a bacteria, yeast, plant, or animal cell. A vector carrying the coding sequence for a recombinant protein under the control of a promoter, such as an expression plasmid, is inserted into a host cell. The promoter controlling the expression of the recombinant gene is then induced and the protein encoded by the recombinant gene is produced within the host cell.

The term "protein purification" refers to a process of purifying a protein and may employ any technique used to separate and isolate a protein of interest to a satisfactory level of purity. Protein purification exploits a protein's various properties such as size, charge, binding affinity, and biological activity. Liquid column chromatography is commonly used in protein purification where a cell lysate containing an expressed protein is passed over a "resin" with particular binding affinity for the protein of interest. A resin is a compound or a polymer with chemical properties that supports the purification of proteins via ion exchange, hydrophobic interaction, size exclusion, reverse phase, or affinity tag chromatography. A protein may also be purified by non-chromatographic techniques such as through the electroporation of protein from an excised piece of a polyacrylamide gel that contained a protein sample of interest.

A "protein tag" refers to an amino acid sequence within a recombinant protein that provides new characteristics to the recombinant protein that assist in protein purification, identification, or activity based on the tag's characteristics and affinity. A protein tag may provide a novel enzymatic property to the recombinant protein such as a biotin tag, or a tag may provide a means of protein identification such as with fluorescence tags encoding for green fluorescent protein or red fluorescent protein. Protein tags may be added onto the N- or C-terminus of a protein. A common protein tag used in protein purification is a poly-His tag where a series of approximately six histidine amino acid residues are added which enables the protein to bind to protein purification matrices chelated to metal ions such as nickel or cobalt. Other tags commonly used in protein purification include chitin binding protein, maltose binding protein, glutathione-S-transferase, and FLAG-tag. Tags such as "epitope tags" may also confer the protein to have an affinity towards an antibody. Common antibody epitope tags include the V5-tag, Myc-tag, and HA-tag.

The terms "fusion protein" or "fused protein" refer to a protein that is coded by a single gene and the single gene is made up of coding sequences that originally coded for at least two or more separate proteins. A fusion protein may retain the functional domains of the two or more separate proteins. Part of the coding sequence for a fusion protein may code for an epitope tag. As described herein for the antibody like protein, a fusion protein may also contain sequences that code for a variety of proteins having varying functional roles based on its application.

The term "protein coding sequence" refers to a portion of a gene that codes for a polypeptide. The coding sequence is located between an ATG initiation of translation codon and the location of a TAG, TAA, or TGA termination of translation codon. Typical to eukaryotic genes, the coding sequence may include the "exons" of a gene, which is the sequence of a gene that is transcribed and translated into a polypeptide, and may exclude the "introns" of a gene, which is the sequence of a gene that is transcribed but not translated into a polypeptide.

The term "transformation" refers to a process of introducing exogenous genetic material into a bacterium by methods employing membrane permeability via chemical or electrical means. Performing a transformation involves adding genetic material, such as a plasmid, to an aliquot of competent bacterial cells, such as E. coli, and allowing the mixture to incubate on ice. The bacterial cells are then either electroporated or placed at 42° C. for approximately 1 minute and then returned to incubate on ice. The bacterial cells are then grown on an agar plate overnight until colonies are visible. The agar plate may contain antibiotic or nutrient conditions for colony selection.

The term "transfection" refers is the process of deliberately introducing nucleic acids into cells. The term is often used for non-viral methods in eukaryotic cells. It may also refer to other methods and cell types, although other terms are preferred: "transformation" is more often used to describe non-viral DNA transfer in bacteria, non-animal eukaryotic cells, including plant cells. In animal cells, transfection is the preferred term as transformation is also used to refer to progression to a cancerous state (carcinogenesis) in these cells. "Transduction" is often used to describe virus-mediated DNA transfer. Nature Methods 2, 875-883 (2005).

The term "Western blot" refers to an analytical technique used to determine the presence of a polypeptide. A Western blot is performed by initially separating proteins on a sodium dodecyl sulfate polyacrylamide gel (SDS-PAGE), and then electro-transferring the separated proteins onto a filter membrane such as a nitrocellulose of PVDF membrane. The membrane is then incubated with a blocking buffer that may contain a blocking agent such as bovine serum albumin or non-fat dry milk. The membrane is then incubated with a primary antibody that is specific for the polypeptide of interest. The primary antibody is washed off from the membrane and the membrane is then incubated with a secondary antibody that is conjugated to a compound or an enzyme that allows for detection and visualization.

The term "homologous sequence" refers to an amino acid or nucleotide sequence that is at least 70% to 99% homologous to a corresponding reference sequence. Sequences that are 90% identical have no more than one different amino acid per 10 amino acids in the reference sequence. The percentage of homology between two or more sequences may be identified using a homology algorithm of Smith and Waterman (1970) Adv. Appl. Math2:482c, Needleman and Wunsch (1970) J. Mol. Biol. 48:433, or Pearson and Lipman (1988) Proc. Natl. Sci. 85:2444. The methods of sequence alignment are known to those in the art. A computer based program employing the mentioned or alternative sequence comparison algorithms may be used such as BLAST as described in The NCBI Handbook (2002) or ClustalOmega as described in Sievers et. al. Mol. Sys. Bio. 7:539 (2011).

The terms "antibody" and "immunoglobulin" are interchangeable and refer to a polypeptide tetramer macromolecule that recognizes and binds, with high affinity and precision, to a binding site referred to as an "epitope" on an antibody target molecule referred to as an "antigen". Antibodies are made up of two identical "heavy chains" and two identical "light chains" referring to the size of each of the individual polypeptide components of an antibody. Each chain is composed of a variable domain and a constant domain, such as the variable heavy and light chains, $V_H$ and $V_L$, respectively, and the constant heavy and light chains, $C_H$ and $C_L$, respectively. The heavy and light chains are interconnected with disulfide bonds to form a Y like structure. The antibody Y like structure can be separated into two regions; the top Fab region and the bottom Fc region. The Fab region contains the variable domains and is responsible for antigen recognition, whereas the Fc region is responsible for inducing effector functions and cellular responses. A review of antibody characteristics and antibody structure is provided in Antibodies: A Laboratory Manual, Second Edition, Cold Spring Harbor Laboratory Press (2013).

The term "fluorescent label" refers to a "fluorophore" that may be covalently attached to a polypeptide or a nucleic acid. Fluorophores absorb light energy at a specific excitation wavelength and re-emit light energy at a specific lower emission wavelength as described by Lakowicz J R. in Principles of Fluorescence Spectroscopy $3^{rd}$ ed. Springer Publishing (2006). Fluorescent labels allow for the detection and localization of a labeled polypeptide or nucleic acid through the use of a microscope that detects fluorescence, a flow cytometer, or any other instrument capable of detecting fluorescence. The labeling, detection, and localization of fluorescently labeled proteins and has been described in detail by Modesti M., Meth. in Mol. Bio. 783:101-20 (2011) and Giepmans et. al., Science 312:5771 (2006). Common fluorophores include but are not limited to Alexa Fluor®, Cy®3 and Cy®5, FITC, TRITC, DAPI, APC, R-PE, and Qdot® as provided by Life Technologies in their Fluorophore Selection guide (www.lifetechnologies.com) and Thermo Scientific (www.piercenet.com).

The term "conserved sequence" refers to a sequence of nucleotides in DNA or RNA, or amino acids in a polypeptide, that are similar across a range of species. Conserved sequences are represented by a nucleotide or an amino acid that occurs at the highest frequency at a particular site in a homologous gene or protein from the same or different species. The term "non-conserved sequence" refers to a sequence of nucleotides or amino acids in a gene or protein that are not conserved and that have a higher variability than conserved sequences.

The term "recombinase protein" refers to any protein or enzyme that is involved in genetic recombination. Recombinase proteins may be involved in various types of genetic recombination events and DNA repair process, such as excision, insertion, inversion, translocation, homologous recombination, or cassette exchange. Recombinase proteins may belong to any family of recombinases, for example, Cre recombinase, Hin recombinase, Tre recombinase, FLP recombinase, Rec recombinase, and integrase family of recombinsases.

The term "two step PCR" refers to a PCR method where a sequence alteration such as a point mutation or introduction/deletion is performed. In a two-step PCR method, A primer set containing the specific DNA alteration and at least 10 bases of 5' complementary overlap are used. The mutagenic primer corresponding to the sense strand of the gene is used as a forward primer coupled with an outer flanking reverse primer. In another concurrent reaction, the corresponding mutagenic "antisense" primer is used a reverse primer with an outer flanking forward primer. The outer primers flanking the DNA of interest should anneal outside the cloning sites to be used for re-introducing the altered DNA back into the vector of choice, or include sequence for required restriction sites if a different destination vector is to be desired.

The term "ligand" refers to any functional group of molecules that form a coordinated interaction with a protein. For example, heparin operates as a ligand with affinity for biomolecules including proteins, lipoproteins, DNA binding proteins, and steroid receptors. A ligand can be immobilized or "coupled" to a solid support such as a base matrix by coupling the ligand via chemical bonds to the base matrix. For example, heparin may be coupled to a Sepharose base matrix. A ligand may be any affinity functional group known to one of ordinary skill in the art. Ligands may be immobilized on resin such as resins used in column chromatography or onto surfaces such as those used in enzyme linked immunosorbent assays (ELISAs).

(ii) Construction of Expression Vectors

The present invention provides for the products and method involving the purification of recombinase proteins, in particular RAD51 and DMC1 proteins, SEQ ID 18 and SEQ ID 21, respectively, of the Rec recombinase family. The genes that encode for the RAD51 or DMC1 may be amplified from any organism, such as from human (for example SEQ ID 12 and SEQ ID 15, respectively) yeast, or bacteria using PCR.

In one exemplary embodiment the gene sequence (SEQ ID 12) coding for the full length human RAD51 protein (SEQ ID 18) may be amplified by PCR, for example by using a forward primer (SEQ 1) and a reverse primer (SEQ 2), wherein SEQ1 and SEQ 2 are ATATATACATATG-GCAATGCAGATGCAGCTTG (RAD51-NdeI_Fwd) and TATATCCTAGGTTATTAGTCTTTGGCATCTC-CCACTCC (RAD51-AvrII Rev), respectively. The amplified RAD51 PCR product may be subsequently cloned between the NdeI and AvrII restriction sites within an expression. Alternative restriction sites sequences may be designed or included in the primers. In yet another embodiment the gene sequence for RAD51 including introns and exons may be cloned. The cloned RAD511 gene may be of the full length sequence as taught in SEQ ID 12 or of any truncated sequence thereof. Alternatively, the cloned full length or truncated RAD51 gene may be tagged at the N- or C-terminus with one or more tags. In yet an alternative embodiment, the cloned RAD51 gene may be mutated at one or more nucleotides.

In another exemplary embodiment the gene sequence (SEQ ID 15) coding for the full length human DMC1 protein (SEQ ID 21) may be amplified PCR, for example by using a forward primer (SEQ 3) and a reverse primer (SEQ 4), wherein SEQ3 and SEQ 4 are AGTTGCCCATAT-GAAGGAGGATCAAGTTGTGG (DMC1-NdeI-Fwd) and GTACAACCTAGGTTATTACTCCTTCGCATCCCCAAT-TCC (DMC1-AvrII-Rev), respectively. The amplified DMC1 PCR product may be subsequently cloned between the NdeI and AvrII restriction sites within an expression vector. Alternative restriction sites sequences may be designed or included in the primers. In yet another embodiment the gene sequence for DMC1 including introns and exons may be cloned. The cloned DMC1 gene may be of the full length sequence as taught in SEQ 15 or of any truncated sequence thereof. Alternatively, the cloned full length or truncated DMC1 gene may be tagged at the N- or C-terminus with one or more tags. In yet an alternative embodiment, the cloned DMC1 gene may be mutated at one or more nucleotides.

In one vector construct embodiment, the pRSFDuet-1 (Novagen) dual expression vector may be used for cloning and co-overexpression of inserted sequences. DNA sequences may be instered into the multiple cloning site of pRSFDuet-1, the multiple cloning site of pRSFDuet-1 is shown in SEQ ID 24. Any dual expression vector may be used. In a preferred embodiment, the sequence for a 6× Histidine-tagged Maltose Binding Protein (MBP) may be inserted between the NcoI and AscI sites of the first open reading frame (ORF1) in the RSFDuet-1 expression vector; designated as the pRSF-Duet1-6×hisMBP vector. In another embodiment, the 6×His or MBP tags may be substituted by alternative tags, such as a Glutathione S-transferase (GST) tag.

Sequences encoding the BRCA2 BRC4 peptide may be PCR amplified with forward primer SEQ 5 and reverse primer SEQ 6, ATTGGGCGCGCCTGGAAAA CCTGT-ATTTTCAGGGATCCAAAGAACCGACCCTGCTG (AscI-BamHI-BRC4-FWD) and AGCTGCGGCCGCTT-ATTAGTCGAACAGGTTTTTAAC (BRC4_D1547-NotI-REV), respectively, and subsequently ligated between AscI and NotI in the pRSF-Duet1-6×hisMBP vector; resulting in a pRSF-Duet1-6×his-MBP-BRC4 vector that encodes a 6×his-MBP-BRC4 fusion protein (SEQ ID 22) transcribed by Open Reading Frame 1 (ORF1). The gene sequence for the 6×his-MBP-BRC4 fusion protein is represented by SEQ ID 16, whereas the protein sequence for the 6×his-MBP-BRC4 fusion protein is represented by SEQ ID 22.

To the pRSF-Duet1-6×his-MBP-BRC4 vector, the RAD51 gene sequence (SEQ ID 12) amplified by SEQ 1 and SEQ 2 primers may be subsequently cloned between the NdeI and AvrII sites of ORF2, producing a pRSF-Duet1-6× his-MBP-BRC4 co hRAD51 cloned construct as shown in FIG. 1. The pRSF-Duet1-6×his-MBP-BRC4 co hRAD51 construct may be transformed into a cell that permits co-overexpression of ORF1 and ORF2, thus co-overexpressing both the 6×his-MBP-BRC4 fusion protein (SEQ ID 22) from ORF1 and the RAD51 protein (SEQ ID 18) from ORF2.

In an alternative embodiment, SEQ ID 16 (the DNA sequence that codes for the 6×his-MBP-BRC4 fusion protein) and SEQ ID 12 (the DNA sequence that codes for the RAD51 protein) may be inserted into any dual expression plasmid under the control of separate promoters or the same promoter. An internal ribosomal entry site (IRES) sequence may be inserted between the 6×his-MB-BRC4 and RAD51 coding sequences. In an alternative embodiment, a "self cleaving" P2A element (such as the T2A, P2A, E2A, F2A protein sequences) may be inserted between the 6×his-MB-BRC4 and RAD51 coding sequences. In yet an alternative embodiment, the DNA sequence that codes for the 6×his-MBP-BRC4 protein and the DNA sequence that codes for the RAD51 protein may be inserted into separate expression plasmids that are in turn transformed into a single cell. The 6×his-MBP-BRC4 fusion protein and the RAD51 protein may be expressed in the same organism or in separate organisms wherein the cell lysate from each organism may be later combined for purification. Alternative versions of SEQ ID 16 and SEW ID 12 that maintain the functionality of the translated protein product as known by one of ordinary skill in the art may also be constructed.

Figure 10:
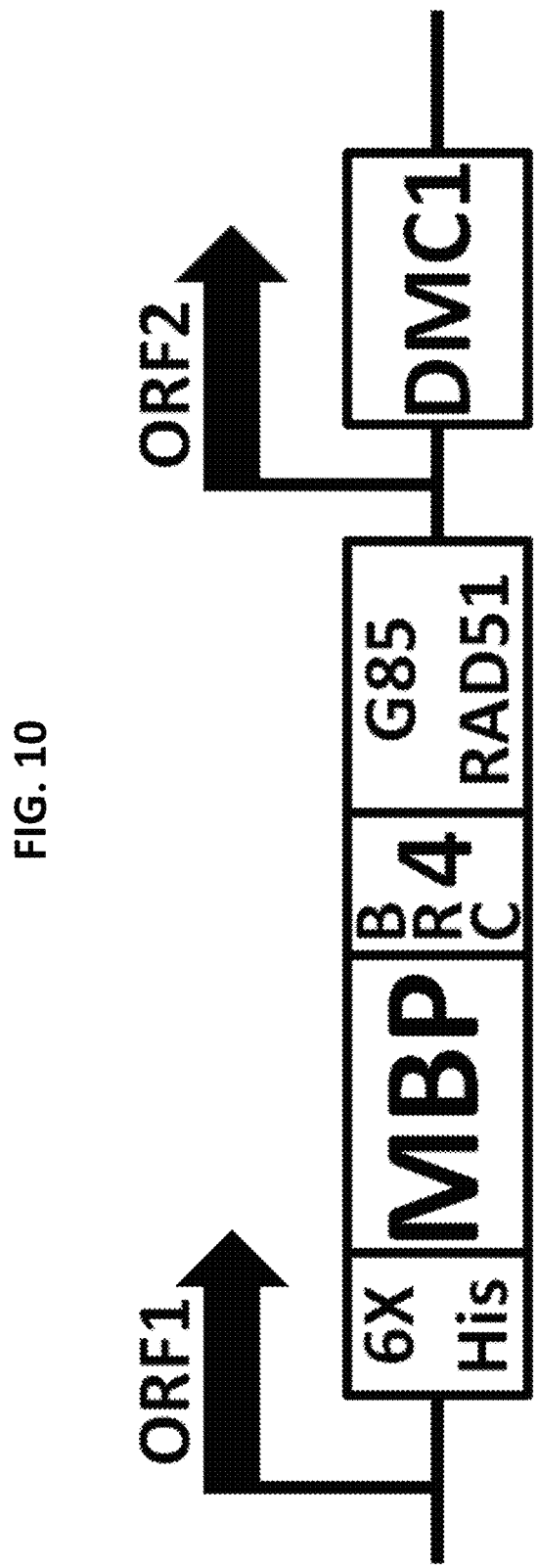
FIG. 10. Diagram representation of vector construct for co-overexpression of 6×his-MBP-tagged-BRC4-G85RAD51 ATPase domain fusion protein from ORF1 and DMC1 protein from ORF2.

In yet another embodiment, a dual expression vector may be constructed with a cloned 6×his-MBP-BCR4-G85RAD51 fusion protein for expression in a first ORF and DMC1 for expression in a second ORF, as shown in FIG. 10, for example in the dual expression vector pRSFDuet-1. To construct the 6×his-MBP-BCR4-G85RAD51 fusion protein construct, RAD51 residues 85-339 may be amplified from a plasmid or genome encoding the RAD51 gene, for example the human RAD51 gene with SEQ 7 and SEQ 8 primers, ACTGCAACTGAATTCCACCAACGTCGCTCAGAGA TCATACAGATTACTACTGG (3×tgs-Rad51G85-fwd) and AGCTGCGGCCGCTTA TCAGTCTTTGGCATCTC-CCACTCC (Rad51-NotI-rev), respectively. SEQ ID 14 represents the gene sequence for human RAD51 residues 85-339. SEQ ID 20 represents the protein sequence for human RAD51 residues 85-339.

BRCA2 residues 1517-1547 may be amplified from plasmid encoding the human BRCA2 gene using SEQ 9 and SEQ 10 primers, GAATAGGATCCAAAGAACCGAC-CCTGCTG (BamHI-BRC4-fwd) and GGAATTCAGTT-GCAGTGGTAAAGCCAGAGCCAGTGCTGCCAGT-GCTGCCAGTGTC GAACAGGTTTTTAAC (3×tgsBRC4-rev), respectively. The two products may be annealed using a 2-step PCR and amplified by flanking SEQ 11 primer; BamHI-BRC4-fwd and Rad51-NotI-rev (AGCTGCGGC-CGCTTATCAGTCTTTGGCATCT CCCACTCC). The resulting product encodes the BRC4 motif of BRCA2 fused to the N-terminal end of Rad51$_{85-339}$ via a 3×Thr-Gly-Ser linker, which is cloned into the BamHI & NotI sites of tev sites of ORF1 of pRSF-Duet1-6×his-MBP to produce pRSF-Duet1-6×his-MBP-BRC4-G85RAD51. The pRSF-Duet1-6×his-MBP-BRC4-G85RAD51 expression vector expresses the 6×His-MBP-BRC4-G85RAD1 fusion protein from ORF1. SEQ ID 17 represents the gene sequence for the 6×His-MBP-BRC4-G85RAD1 fusion protein. SEQ ID 23 represents the protein sequence for the 6×His-MBP-BRC4-G85RAD1 fusion protein. SEQ ID 13 represents the gene sequence for BRC4. SEQ ID 19 represents the protein sequence for BRC4.

Figure 11:
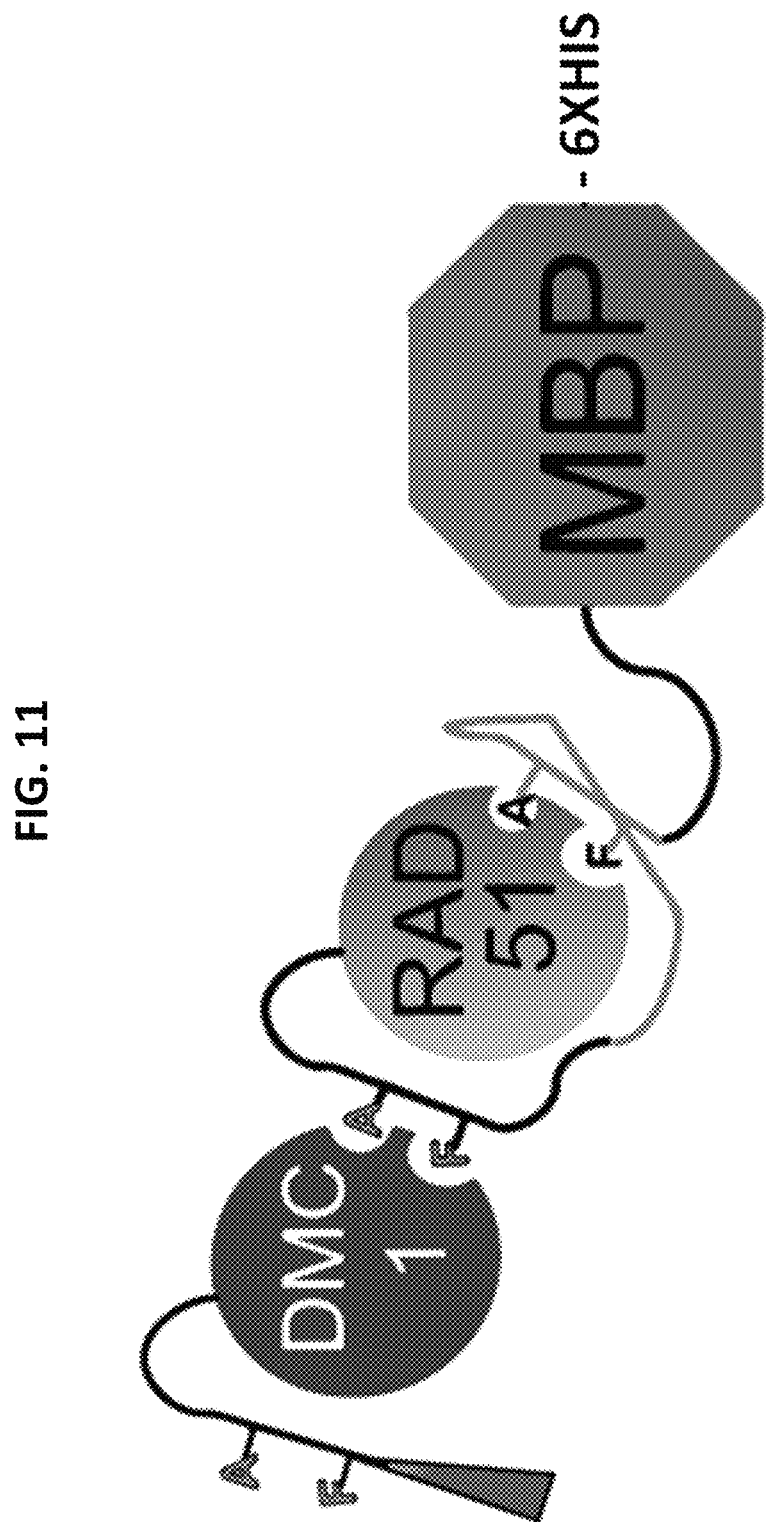
FIG. 11. Representation of DMC1 protein interacting with the G85RAD51 F-X-X-A motif in the 6×his-MBP-tagged-BRC4-G85RAD51 ATPase domain fusion protein.

The DMC1 gene (SEQ ID 15) amplified by primers SEQ 3 and SEQ4 may be ligated between the NdeI and AvrII sites of the $2^{nd}$ ORF of pRSF-Duet1-6×his-MBP-BRC4-G85RAD51, creating an expression vector (of pRSF-Duet1-6×his-MBP-BRC4-G85RAD51 co DMC1) wherein the 6×His-MBP-BRC4-G85RAD1 fusion protein (SEQ ID 23) may be co-overexpressed with DMC1 protein (SEQ ID 21) as shown in FIG. 10. Once the DMC1 protein and the 6×His-MBP-BRC4-G85RAD1 fusion protein are co-overexpressed, the DMC1 protein interacts with the G85RAD51 F-X-X-A repeat motif of the ATPase domain in the 6×His-MBP-BRC4-G85RAD1 fusion protein as shown in FIG. 11.

In an alternative embodiment, the DNA sequence (SEQ ID 17) that codes for the 6×His-MBP-BRC4-G85RAD1 fusion protein and the DNA sequence (SEQ ID 15) that encodes for the DMC1 protein may be inserted into any dual expression plasmid under the control of separate promoters or the same promoter. For example, an internal ribosomal entry site (IRES) sequence may be inserted between the 6×his-MBP-BRC4-G85RAD51 and DMC1 coding sequences. In an alternative embodiment, a "self cleaving" P2A element (such as the T2A, P2A, E2A, F2A protein sequences) may be inserted between the 6×his-MB-BRC4 and RAD51 coding sequences. In yet an alternative embodiment, the DNA sequence that codes for the 6×His-MBP-BRC4-G85RAD1 fusion protein and the DNA sequence that codes for the DMC1 protein may be inserted into separate expression plasmids that are in turn transformed into a single cell. The 6×His-MBP-BRC4-G85RAD1 fusion protein and the DMC1 protein may be expressed in the same organism or in separate organisms wherein the cell lysate from each organism may be later combined for purification.

(iii) Purification of RAD51

All recombinant protein expression may be initiated from fresh overnight transformation of *E. coli* strain BL21, harboring the pRARE plasmid (chloramphenicol resistance), with the co-overexpression plasmid (for example, with the pRSF-Duet1-6×his-MBP-BRC4 co RAD51 vector). An entire plate of freshly formed colonies is then scraped and used to seed a starter culture (Turbo Broth culture medium—Athena Enzyme Systems) supplemented with the appropriate antibiotic (routinely both kanamycin and chloramphenicol). A starter culture of may be prepared in an orbital shaker (shaking at an rpm of 180-200 rpm at 37° C.) that is grown to reach an $OD_{600} \geq 1.0$. A volume of the dense starter culture is then used to seed each liter of culture grown (for example 1 L Turbo broth, in 2 L dimpled shake flasks, 8 L total) and allowed to reach $OD_{600} \geq 1.0$. Any volume of culture may be grown for overexpression. At $OD_{600} \geq \sim 1$, over-expression is induced by addition of IPTG, for example a concentration of 200 μM IPTG may be used. The recombinant proteins, such as 6×his-MBP-BRC4 fusion protein and the RAD51 protein are overexpressed upon the addition of IPTG. After induction the cell cultures may be grown for an appropriate amount of time to overexpress protein from the induced promoter. For example, cells may be grown for 3 hours at 37° C. while shaking or for 15 hours or overnight at 15° C. while shaking.

Once the 6×his-MBP-BRC4 fusion protein and the RAD51 protein are overexpressed, the cells are harvested. Harvesting of cell cultures may be performed by centrifugation, for example centrifugation at 4,200 rpm for 30 minutes at 4° C. The cell pellet may then be lysed in a stabilizing buffer or in cell lysis buffer. An example of cell lysis buffer is 20 mM Tris pH 8.0, 500 mM NaCl, 20 mM imidazole. Additives such as carbohydrates, lysozyme, detergents, reducing agents, or protease inhibitors (such as SIGMAfast™ EDTA-free Protease inhibitor tablets) may be added to the lysis buffer. Cell lysis may be performed using any cell lysis method known by one of ordinary skill in the art. For example, cells may be lysed via a lysis buffer, French Press, sonication, high pressure homogenization (for example an Avestin EmulsiFlex-C5 high pressure homogenizer), jet milling, bead milling, or freeze thaw cycles. In a preferred embodiment, cells are lysed by flash freezing in liquid $N_2$.

The cell lysate may be filtered or centrifuged to separate insoluble cell debris and precipitated debris from soluble protein such as the 6×his-MBP-BRC4 fusion protein and the RAD51 protein. In a preferred embodiment, the cell lysate may be centrifuged at 30,000 g for 1 hour at 4° C. After centrifugation, the supernatant may be passed through a filter, for example a 5 μm filter, to remove any remaining insoluble particles in preparation for column chromatography. After centrifugation and/or filtration, the soluble protein (referred to as the cell extract), is applied to a chromatography resin, for example a resin specific to the affinity tag that is fused to the BRC4 repeat motif.

Figure 2:
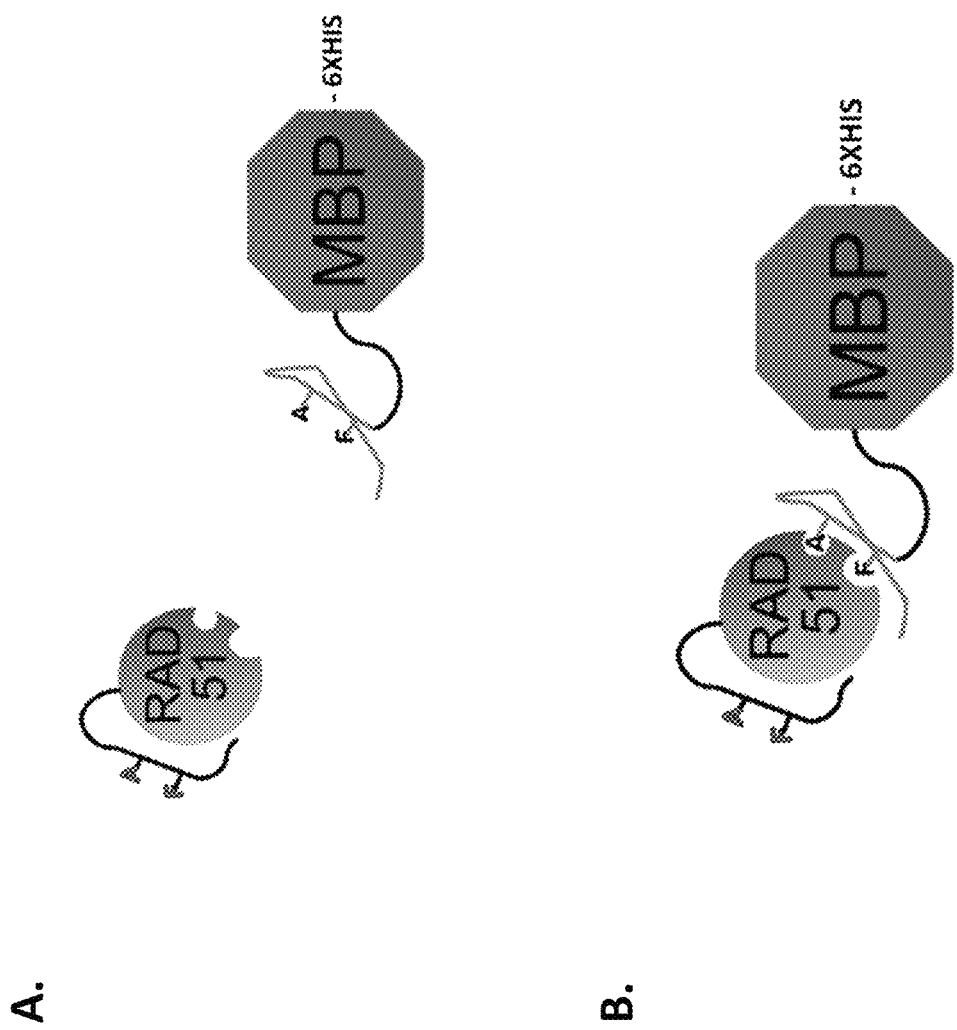
FIG. 2A. Representation of 6×his-MBP-tagged-BRC4 and RAD51 proteins.
FIG. 2B. Representation of the F-X-X-A motif in the 6×his-MBP-tagged-BRC4 fusion protein interacting with RAD51.
Figure 3:
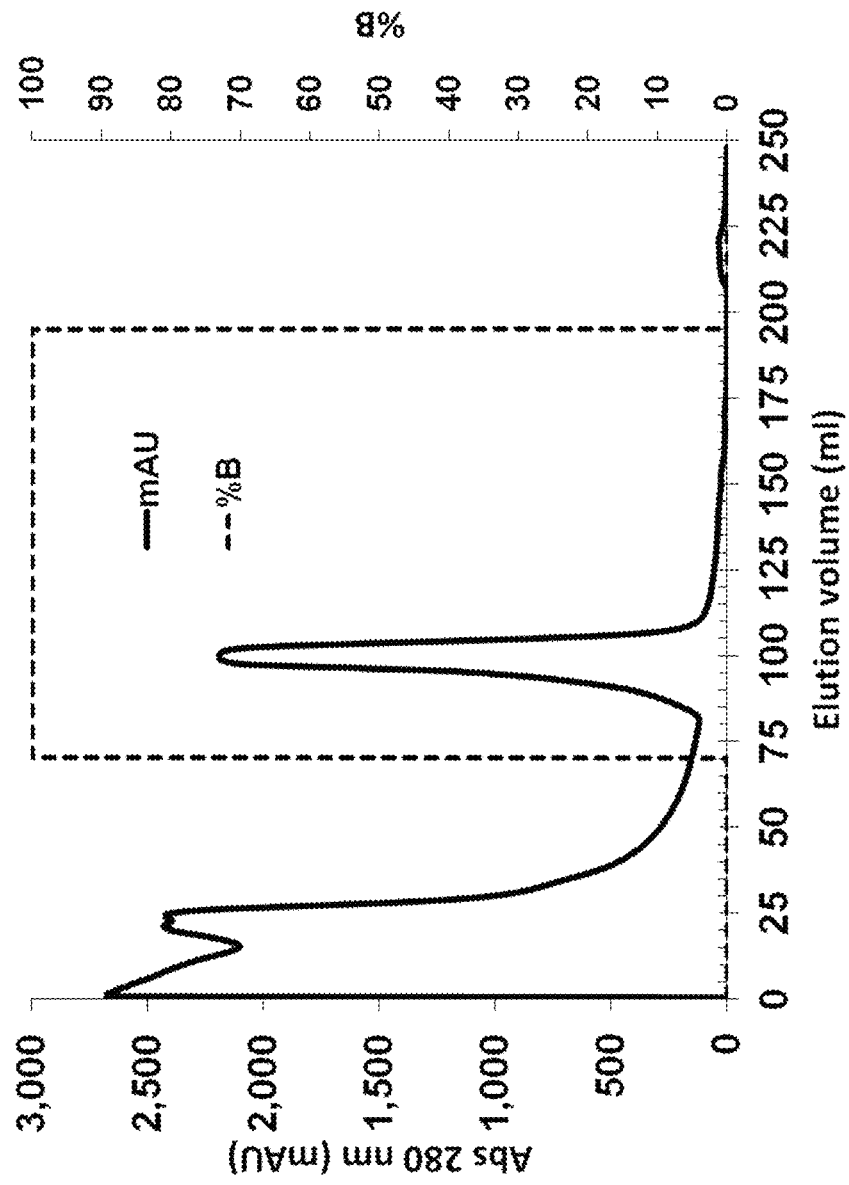
FIG. 3. Elution profile of RAD51 protein purification via $Ni^{2+}$-NTA affinity resin using a step gradient of increasing Imidazole concentration (% B) as the eluent.

The co-overexpressed 6×his-MBP-BRC4 fusion protein and the RAD51 protein shown in FIG. 2A interact and form protein-protein bonds with each other as shown in FIG. 2B, permitting for their co-purification. For example, purification of the 6×his-MBP-BRC4 fusion protein and RAD51 protein from cell extract may be achieved by applying the cell extract to a resin containing immobilized NTA resin, such as Sepharose HP Hi-Trap™ resin (GE Healthcare Life Sciences), charged with $Ni^{2+}$. A purification system, such as an ÄKTA Protein Purification System (GE Healthcare Life Sciences), may be used for protein purification. Alternatively, the tagged fusion protein and recombinase may be purified using an immobilized ligand. The 6× histidine tag in the 6×his-MBP-BRC4 fusion protein binds to the $Ni^{2+}$-NTA resin while concurrently the BRC4 motif binds to the RAD51 protein. The bound proteins may be washed with a wash buffer, for example a wash buffer containing 20 mM Tris pH 8.0, 500 mM NaCl, 20 mM Imidazole. The 6×his-MBP-BRC4 fusion protein along with the RAD51 protein may then be eluted from the $Ni^{2+}$-NTA resin using increasing concentration of imidazole as shown in FIG. 3, wherein the mAU peak at 100% B is the elution of the 6×his-MBP-BRC4 fusion protein bound to the RAD51 protein. The elution buffer may be 20 mM Tris pH 8.0, 500 mM NaCl, 200 mM imidazole.

Figure 4:
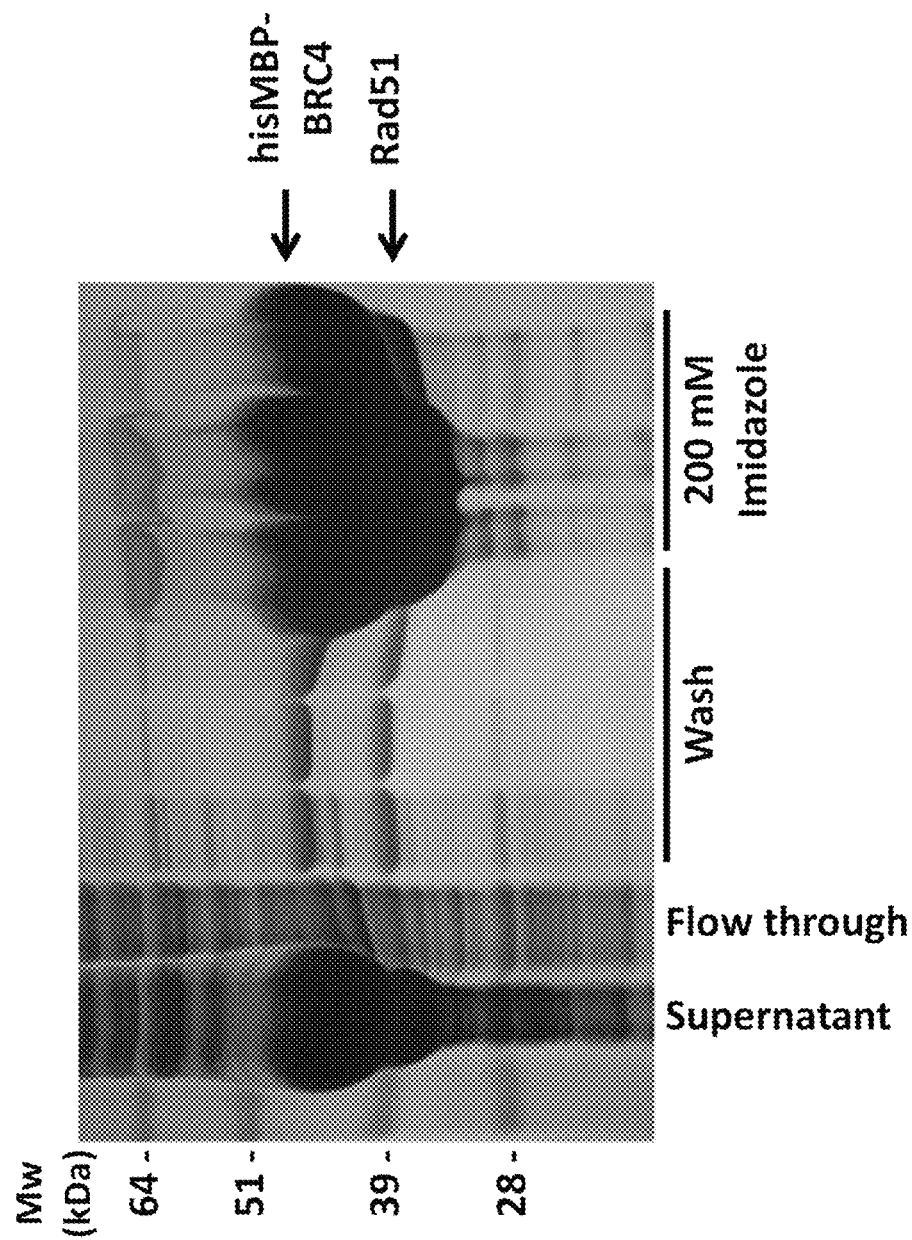
FIG. 4. Coomassie stained SDS-PAGE gel of various elution fractions obtained in RAD51 purification via the $Ni^{2+}$-NTA affinity resin shown in FIG. 3.

FIG. 4 is a Coomassie stained SDS-PAGE gel of various elution fractions obtained from the $Ni^{2+}$-NTA affinity chromatography shown in FIG. 3. FIG. 4 shows that the RAD51 protein bound to the 6×his-MBP-BRC4 fusion protein co-eluted in the 200 mM imidazole fraction. Peak fractions containing the RAD51 protein bound to the 6×his-MBP-BRC4 fusion protein may be pooled together.

In one embodiment, the pooled fractions containing the RAD51 protein bound to the 6×his-MBP-BRC4 fusion protein may then be loaded onto an amylose resin that binds to MBP. The 6×his-MBP-BRC4 fusion protein (along with the associated RAD51 protein) binds to the amylose resin. The bound protein my then be washed with wash a wash buffer, for example 20 mM Tris pH 8.0, 500 mM NaCl. Bond protein may then be eluted with elution buffer, for example with 20 mM Tris, pH 8.0, 500 mM NaCl, and 20 mM maltose. In another embodiment, if the fusion protein construct was designed with an alternative protein tag, for example a GST tag, then an alternative affinity resin may be used specific for the alternative tag, for example glutathione Sepharose resin wherein glutathione would be used to elute bound tagged fusion protein along with proteins associated via protein-protein to the fusion tagged protein.

In another embodiment, following elution of the 6×his-MBP-BRC4 fusion protein and RAD51 protein from the $Ni^{2+}$-NTA affinity resin, the pooled fractions may be processed by exchanging the sample buffer into a low salt buffer, for example by overnight dialyzing the pooled fractions using a dialysis membrane (for example a 6,000-8000 MWCO dialysis membrane) at 4° C. The said low salt buffer may be Tris pH 8.0, containing 50 mM NaCl.

In yet another embodiment, following elution of the 6×his-MBP-BRC4 fusion protein and RAD51 protein from the $Ni^{2+}$-NTA affinity resin, the pooled fractions may be diluted with a buffer, for example diluted 5-fold with 20 mM Tris pH 8.0, resulting in a sample with a NaCl concentration of near 100 mM.

Figure 5:
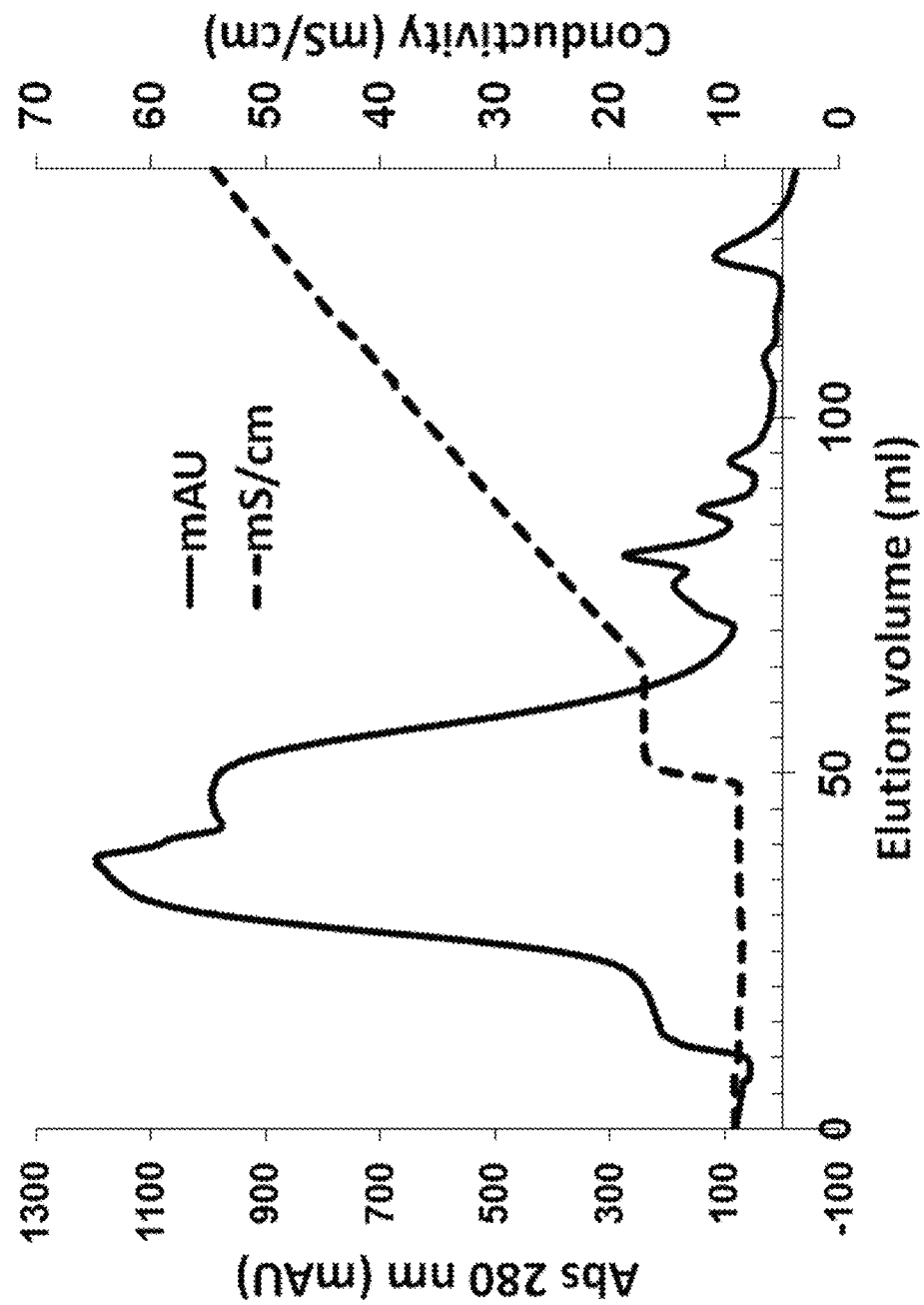
FIG. 5. Elution profile of RAD51 protein purification via affinity to heparin using a step and gradual increasing NaCl concentration as the eluent.

The dialyzed protein sample in low salt buffer may then be applied to a chromatography resin containing an immobilized molecule that is known to generally mimic DNA molecules. One exemplary molecule is the heparin ligand which is known to one with ordinary skill in the art to efficiently bind to a variety of DNA binding proteins. For example, the dialyzed protein may be applied to a Heparin Sepharose HiTrap™ HF resin (GE Healthcare Life Science). The RAD51 protein has biding specificity to the heparin ligand and will bind to the heparin ligand along with the bound 6×his-MBP-BRC4 fusion protein. Increasing the NaCl concentration, for example from 0.1 to 1.0 M, will elute proteins bound to the heparin ligand. The heparin ligand with bound protein may be washed with a wash buffer, for example 20 mM Tris pH 8.0 and 200 mM, followed by elution with a linear 0.2 M-0.7 M NaCl gradient as shown in FIG. 5. The 6×his-MBP-BRC4 fusion protein will elute early in the NaCl gradient, while RAD51 will elute near 600 mM NaCl as shown in FIG. 5.

Figure 6:
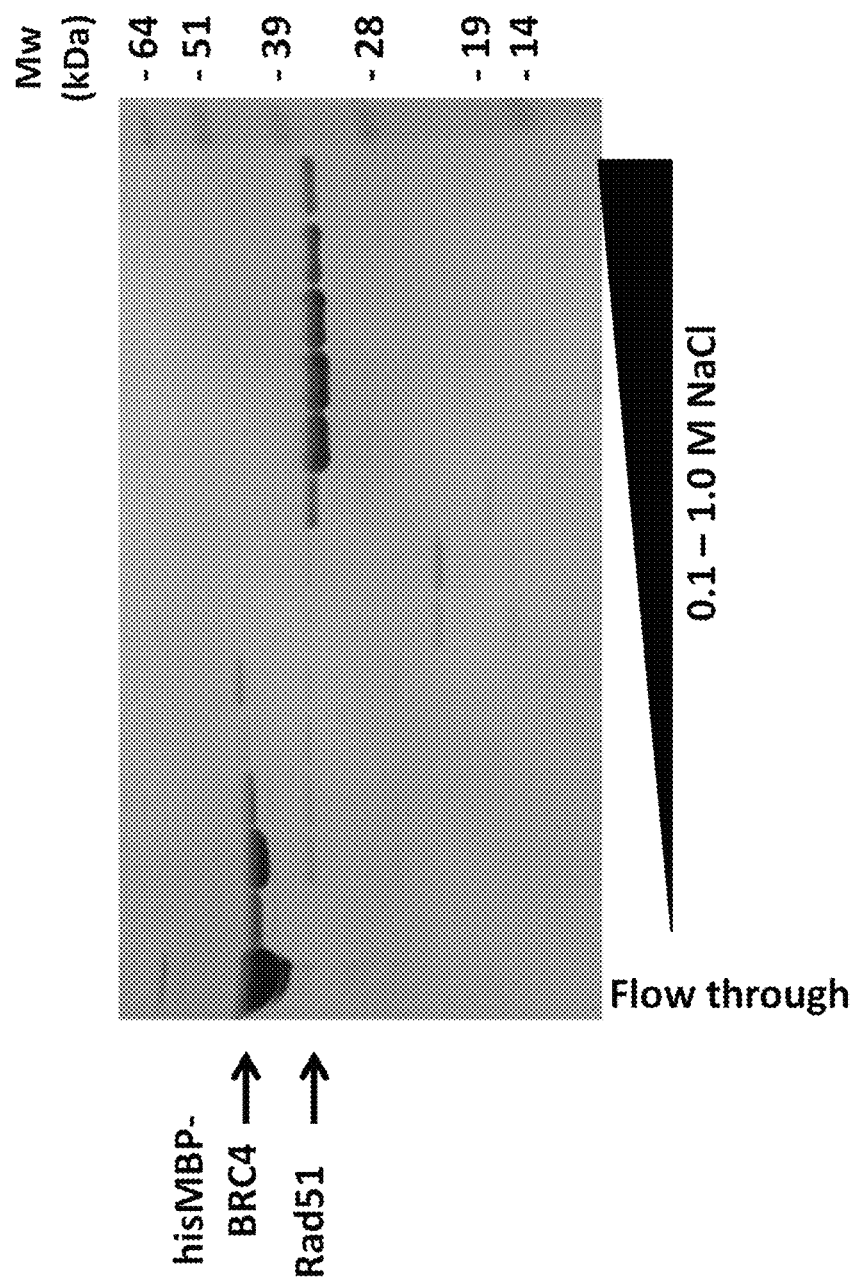
FIG. 6. Coomassie stained SDS-PAGE gel of various elution fractions obtained in RAD51 purification via heparin affinity shown in FIG. 5.

FIG. 6 is a Coomassie stained SDS-PAGE gel of various elution fractions obtained from the heparin affinity chromatography shown in FIG. 5. FIG. 6 shows that the 6×his-MBP-BRC4 fusion protein eluted early in the NaCl gradient, whereas the RAD51 protein bound eluted near 600 mM NaCl. Peak fractions containing the RAD51 protein may be pooled together.

The pooled RAD51 protein may be concentrated by any protein concentration means. For example, protein may be concentrated using centrifugal filters units with Molecular Weight Cut Off filters specific to the protein of interest. Protein may be concentrated using any ultrafiltration or depth filtration technique.

Figure 7:
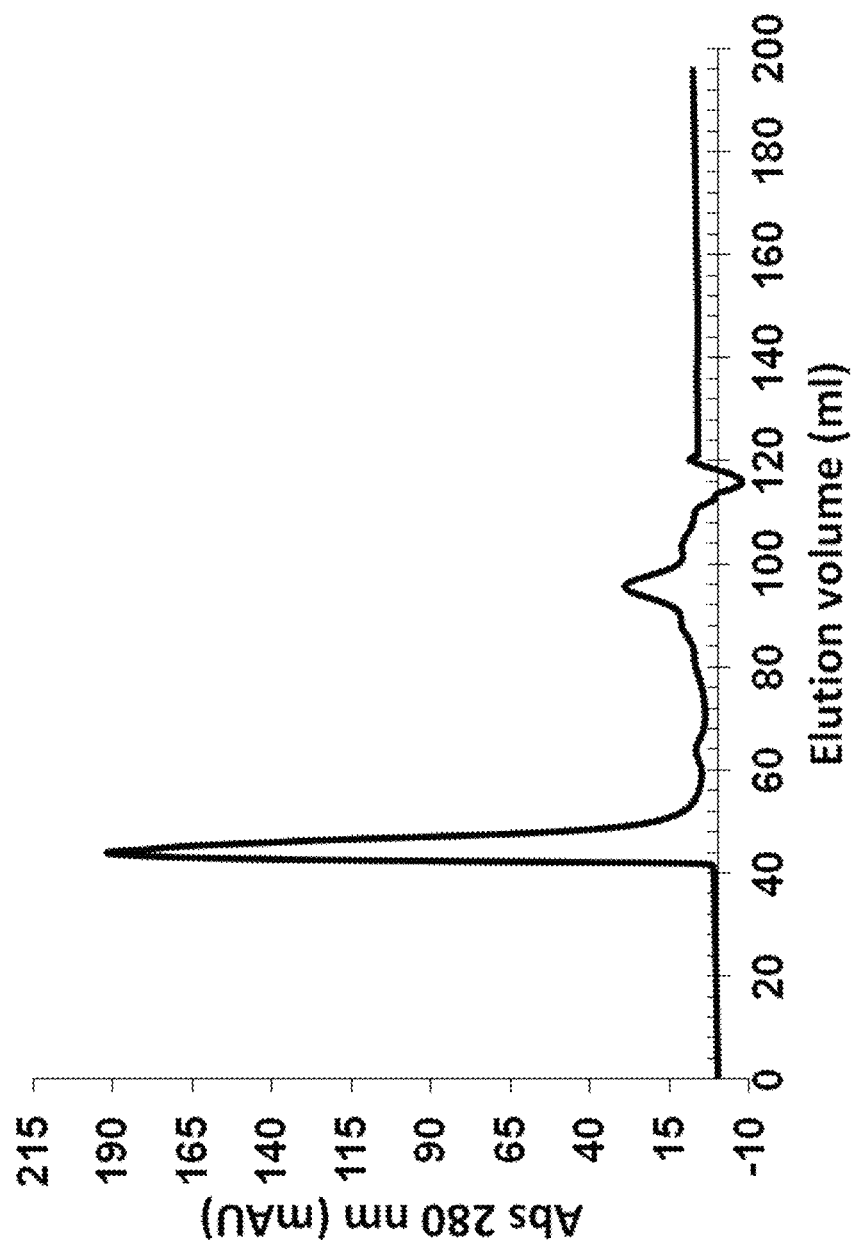
FIG. 7. Elution profile of RAD51 protein purification via a Superdex 200 size exclusion resin.

The pooled fractions containing the purified RAD51 protein may then be applied onto a size exclusion resin (also known referred to as a gel filtration resin), for example, Superdex 200 resin. The size exclusion resin may be equilibrated with an equilibration buffer, such as 20 mM Tris pH 8.0, 300 mM NaCl prior to injection of the RAD 51 sample. FIG. 7 shows an elution profile of RAD51 applied to a Superdex size exclusion column; oligomeric RAD51 elutes from the column largely in the void volume. Any other size exclusion/gel filtration resin or resin used to separate proteins based on size and or shape may be used.

Figure 8:
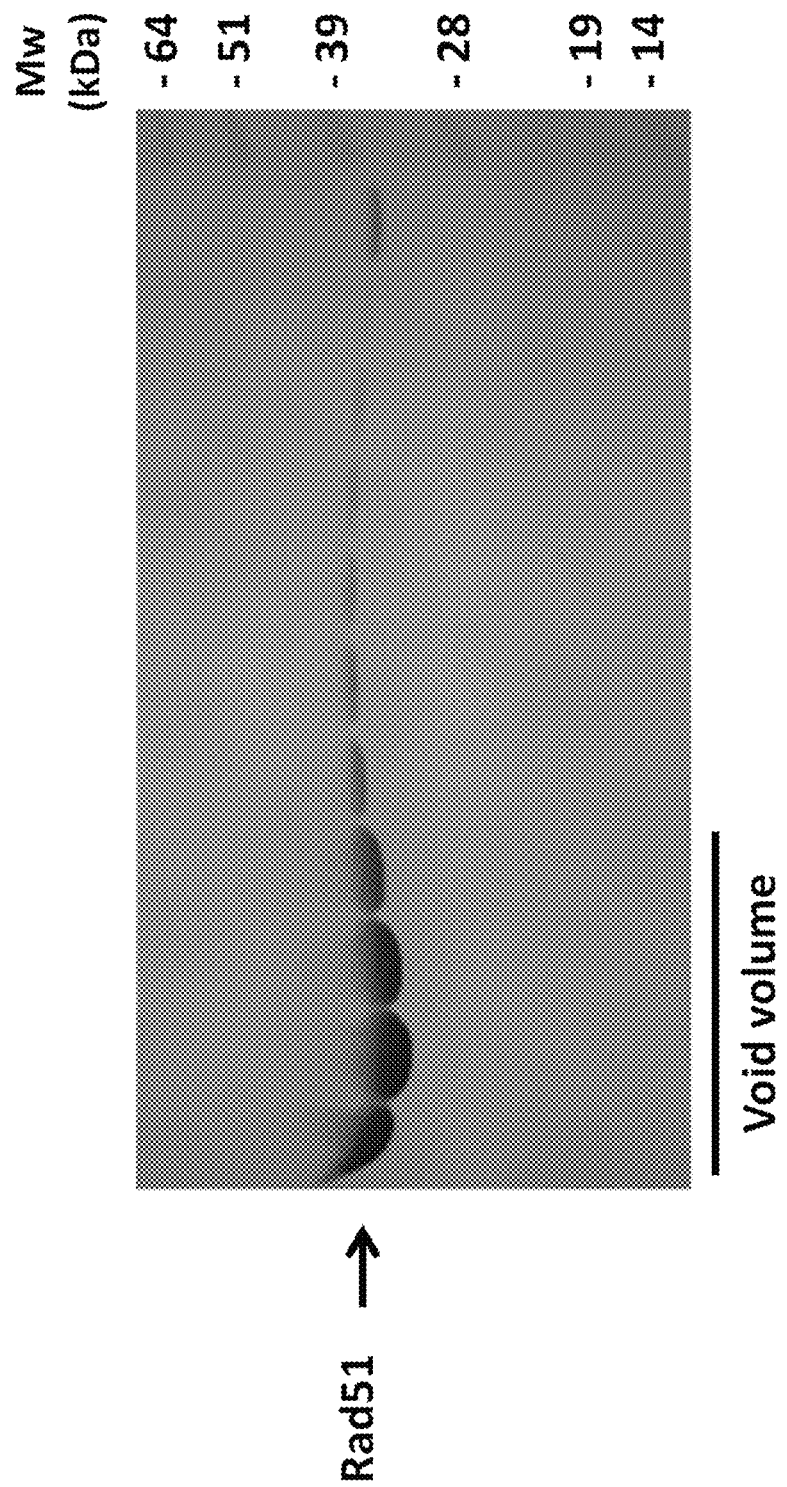
FIG. 8. Coomassie stained SDS-PAGE gel of various elution fractions obtained in RAD51 purification via the Superdex 200 size exclusion resin in FIG. 7.

FIG. 8 is a Coomassie stained SDS-PAGE gel of various elution fractions obtained from the Superdex 200 size exclusion chromatography shown in FIG. 7. FIG. 8 shows that the RAD51 protein eluted predominantly in the void volume. Peak fractions containing the RAD51 protein may be pooled together.

Any buffer additive such as DTT (for example 1 mM final DTT concentration) may be added to the purified RAD51 sample. The pooled RAD51 protein may be concentrated and snap frozen in liquid $N_2$ for storage in a freezer, for example at −80° C. The pooled RAD51 protein may also be stabilized in a buffer for storage at room temperature, or lyophilized, or prepared for storage in any storage means known by one of ordinary skill in the art.

Figure 9:
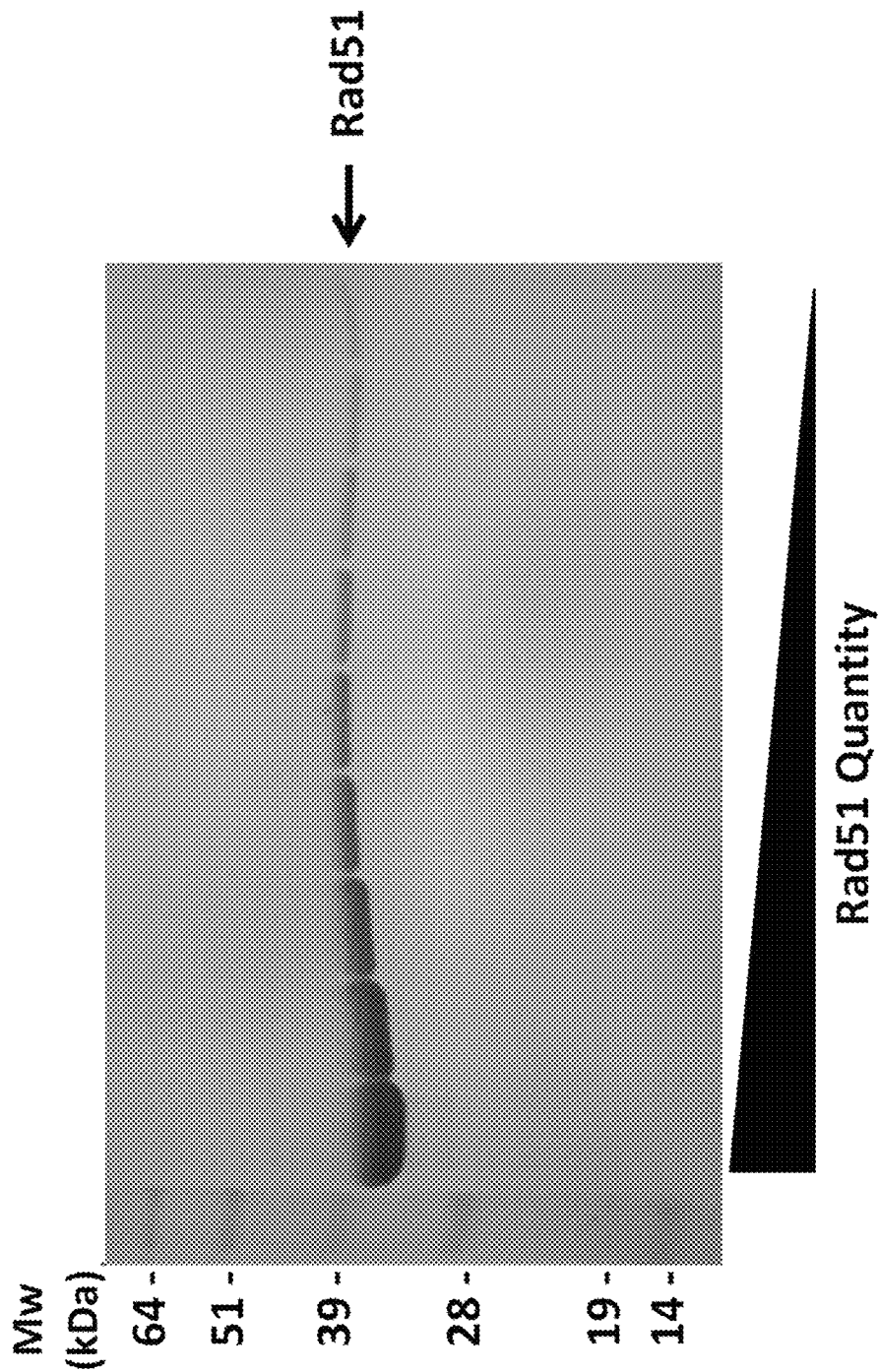
FIG. 9. Coomassie stained SDS-PAGE of final purified RAD51 protein loaded in decreasing concentration from left to right.

FIG. 9 is a Coomassie stained SDS-PAGE gel of the final RAD51 protein product loaded in decreasing concentration. Results show a highly pure RAD51 protein.

The purification of RAD51 may be performed in any sequential combination of chromatography resins as described herein as known by one with ordinary skill in the art.

(iv) Purification of DMC1

All recombinant protein expression may be initiated from fresh overnight transformation of *E. coli* strain BL21, harboring the pRARE plasmid (chloramphenicol resistance), with the co-overexpression plasmid, such as the pRSF-Duet1-6×his-MBP-BRC4-G85RAD51 co DMC1 vector. An entire plate of freshly formed colonies is then scraped and used to seed a starter culture (Turbo Broth culture medium—Athena Enzyme Systems) supplemented with the appropriate antibiotic (routinely both kanamycin and chloramphenicol). A starter culture of may be prepared in an orbital shaker (shaking at an rpm of 180-200 rpm at 37° C.) that is grown to reach an $OD_{600} \geq 1.0$. A volume of the dense starter culture is then used to seed each liter of culture grown (for example 1 L Turbo broth, in 2 L dimpled shake flasks, 8 L total) and allowed to reach $OD_{600} \geq 1.0$. Any volume of culture may be grown for overexpression. At $OD_{600} \geq \sim 1$, over-expression is induced by addition of IPTG, for example a concentration of 200 μM IPTG may be used. The recombinant proteins, such as 6×His-MBP-BRC4-G85RAD1 fusion protein and the DMC1 protein are overexpressed upon the addition of IPTG. After induction the cell cultures may be grown for an appropriate amount of time to overexpress protein from the induced promoter. For example, cells may be grown for 3 hours at 37° C. while shaking or for 15 hours or overnight at 15° C. while shaking.

Once the 6×His-MBP-BRC4-G85RAD1 fusion protein and the DMC1 protein are overexpressed, the cells are harvested. Harvesting of cell cultures may be performed by centrifugation, for example centrifugation at 4,200 rpm for 30 minutes at 4° C. The cell pellet may then be lysed in a stabilizing buffer or in cell lysis buffer. An example of cell lysis buffer is 20 mM Tris pH 8.0, 500 mM NaCl, 20 mM imidazole. Additives such as carbohydrates, lysozyme, detergents, reducing agents, or protease inhibitors (such as SIGMAfast™ EDTA-free Protease inhibitor tablets) may be added to the lysis buffer. Cell lysis may be performed using any cell lysis method known by one of ordinary skill in the art. For example, cells may be lysed via a lysis buffer, French Press, sonication, high pressure homogenization (for example an Avestin EmulsiFlex-C5 high pressure homogenizer), jet milling, bead milling, or freeze thaw cycles. In a preferred embodiment, cells are lysed by flash freezing in liquid $N_2$.

The cell lysate may be filtered or centrifuged to separate insoluble cell debris and precipitated debris from soluble protein such as the 6×His-MBP-BRC4-G85RAD1 fusion protein and the DCM1 protein. In a preferred embodiment, the cell lysate may be centrifuged at 30,000 g for 1 hour at 4° C. After centrifugation, the supernatant may be passed through a filter, for example a 5 μm filter, to remove any remaining insoluble particles in preparation for column chromatography. After centrifugation and/or filtration, the soluble protein (referred to as the cell extract), is applied to a chromatography resin, for example a resin specific to the affinity tag that is fused to the BRC4 repeat motif.

The co-overexpressed 6×His-MBP-BRC4-G85RAD1 fusion protein and the DMC1 protein interact and form protein-protein bonds with each other as shown in FIG. 11, permitting for their co-purification. For example, purification of the 6×His-MBP-BRC4-G85RAD1 fusion protein and DMC1 protein from cell extract may be achieved by applying the cell extract to a resin containing immobilized NTA resin, such as Sepharose HP Hi-Trap™ resin (GE Healthcare Life Sciences), charged with $Ni^{2+}$. A purification system, such as an ÄKTA Protein Purification System (GE Healthcare Life Sciences), may be used for protein purification. The 6× histidine tag in the 6×His-MBP-BRC4-G85RAD1 fusion protein binds to the $Ni^{2+}$-NTA resin while concurrently the RAD51 F-X-X-A ATPase motif in G85RAD51 binds to the DMC1 protein. The bound proteins may be washed with a wash buffer, for example a wash buffer containing 20 mM Tris pH 8.0, 500 mM NaCl, 20 mM Imidazole. The 6×His-MBP-BRC4-G85RAD1 fusion protein along with the DMC1 protein may then be eluted from the $Ni^{2+}$-NTA resin using increasing concentration of imidazole (not shown), wherein the mAU peak at 100% B is the elution of the 6×His-MBP-BRC4-G85RAD1 fusion protein bound to the DMC1 protein. The elution buffer may be 20 mM Tris pH 8.0, 500 mM NaCl, 200 mM imidazole.

In one embodiment, the pooled fractions containing the DMC1 protein bound to the 6×His-MBP-BRC4-G85RAD1 fusion protein may then be loaded onto an amylose resin that binds to MBP. The 6×His-MBP-BRC4-G85RAD1 fusion protein (along with the associated DMC1 protein) binds to the amylose resin. The bound protein my then be washed with wash a wash buffer, for example 20 mM Tris pH 8.0, 500 mM NaCl. Bound protein may then be eluted with elution buffer, for example with 20 mM Tris, pH 8.0, 500 mM NaCl, and 20 mM maltose.

Figure 12:
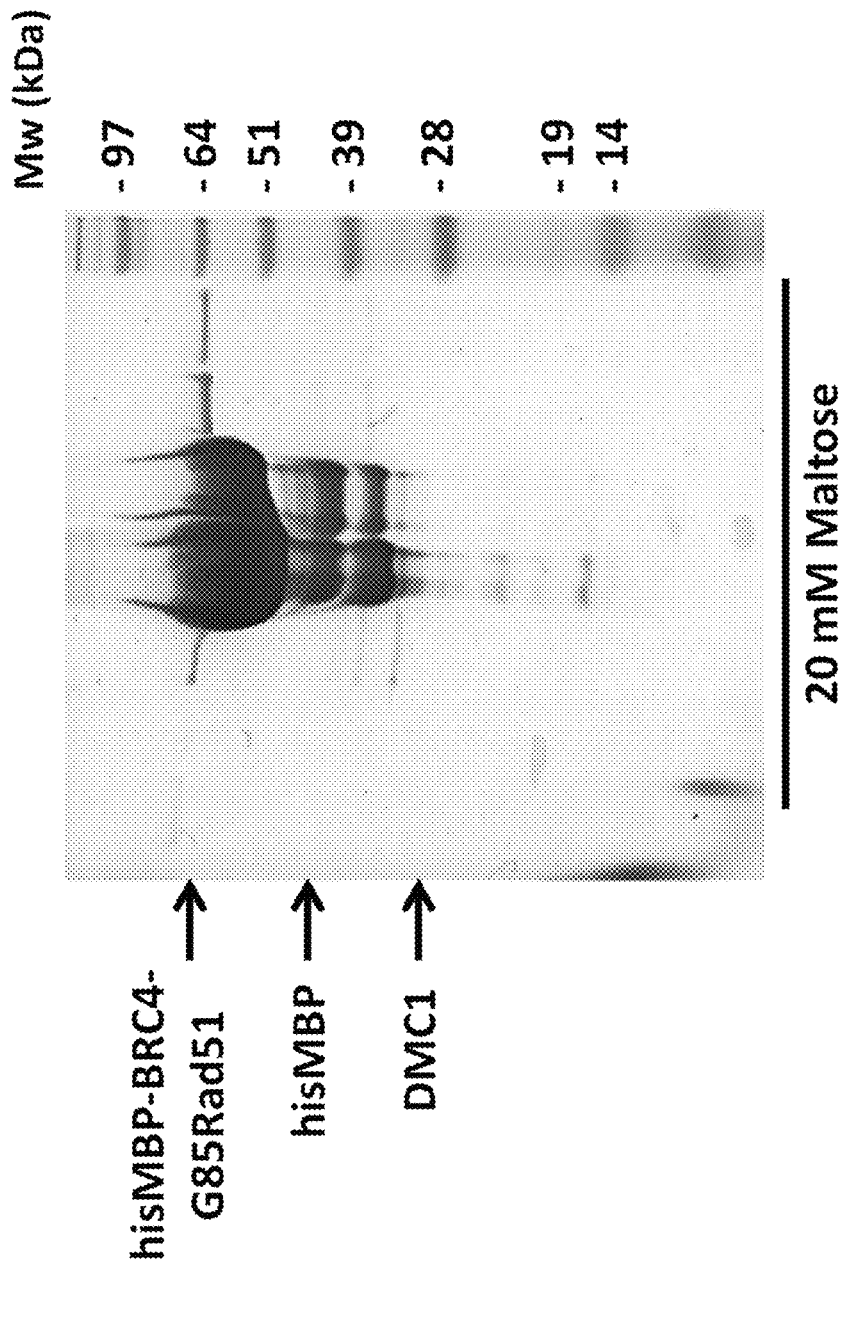
FIG. 12. Coomassie stained SDS-PAGE gel showing purification of DMC1 protein and 6×his-MBP-tagged-BRC4-G85RAD51 ATPase domain fusion protein via MBP-tag affinity using immobilized amylose.

FIG. 12 is a coomassie stained SDS-PAGE gel of various elution fractions of 6×His-MBP-BRC4-G85RAD1 fusion protein and DMC1 protein obtained from the amylose resin chromatography. FIG. 12 shows that the DMC1 protein co-eluted with the 6×His-MBP-BRC4-G85RAD1 fusion protein in 20 mM maltose. Peak fractions containing the DMC1 protein may be pooled together.

In another embodiment, if the fusion protein construct was designed with an alternative protein tag, for example a GST tag, then an alternative affinity resin may be used specific for the alternative tag, for example Glutathione Sepharose resin wherein glutathione would be used to elute bound tagged fusion protein along with proteins associated via protein-protein to the fusion tagged protein.

Following elution of the 6×His-MBP-BRC4-G85RAD1 fusion protein and DMC1 protein from the $Ni^{2+-}$NTA affinity resin, the pooled fractions may be processed by exchanging the sample buffer into a low salt buffer, for example by overnight dialyzing the pooled fractions using a dialysis membrane (for example a 6,000-8000 MWCO dialysis membrane) at 4° C. The said low salt concentration buffer may be Tris pH 8.0, containing 50 mM NaCl.

In yet another embodiment, following elution of the 6×His-MBP-BRC4-G85RAD1 fusion protein and DMC1 protein from the $Ni^{2+-}$NTA affinity resin, the pooled fractions may be diluted with a buffer, for example diluted 5-fold with 20 mM Tris pH 8.0, resulting in a sample with a NaCl concentration of near 100 mM.

The dialyzed protein sample in low salt buffer may then be applied to a chromatography resin containing an immobilized molecule that is known to generally mimic DNA molecules. One exemplary molecule is heparin which is known to one with ordinary skill in the art to efficiently bind to a variety of DNA binding proteins. For example, the dialyzed protein may be applied to a Heparin Sepharose HiTrap™ HF resin (GE Healthcare Life Science). The DMC1 protein has biding specificity to the heparin ligand and will bind to the heparin ligand along with the bound 6×His-MBP-BRC4-G85RAD1 fusion protein. Increasing the NaCl concentration, for example from 0.1 to 1.5 M, will elute proteins bound to the heparin ligand. The heparin ligand with bound protein may be washed with a wash buffer, for example 20 mM Tris pH 8.0 and 200 mM, followed by elution with a linear 0.2 M-0.7 M NaCl gradient as shown in FIG. 5. The 6×His-MBP-BRC4-G85RAD1 fusion protein will elute early in the NaCl gradient, while DMC1 will elute near 600 mM NaCl as shown in heparin affinity chromatography elution profile FIG. 13.

Figure 13:
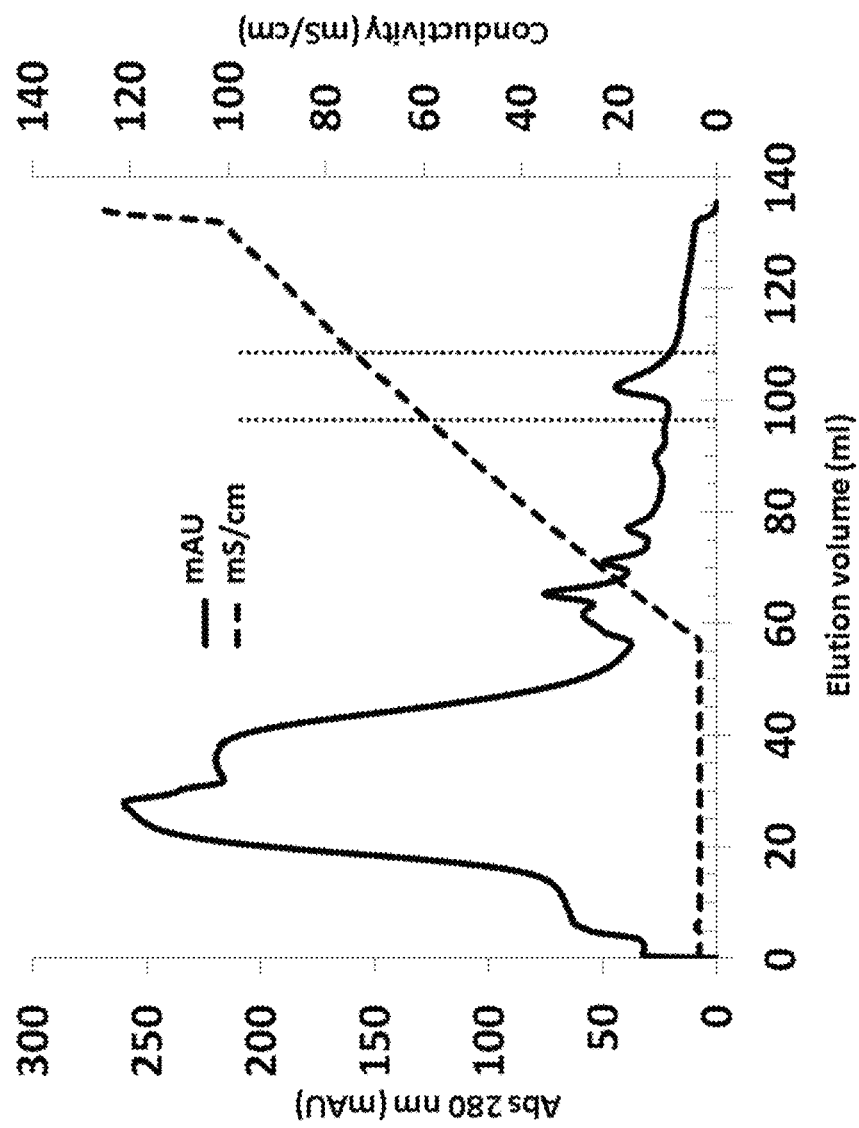
FIG. 13. Elution profile of DMC1 protein purification via affinity to heparin using an increasing NaCl concentration.
Figure 14:
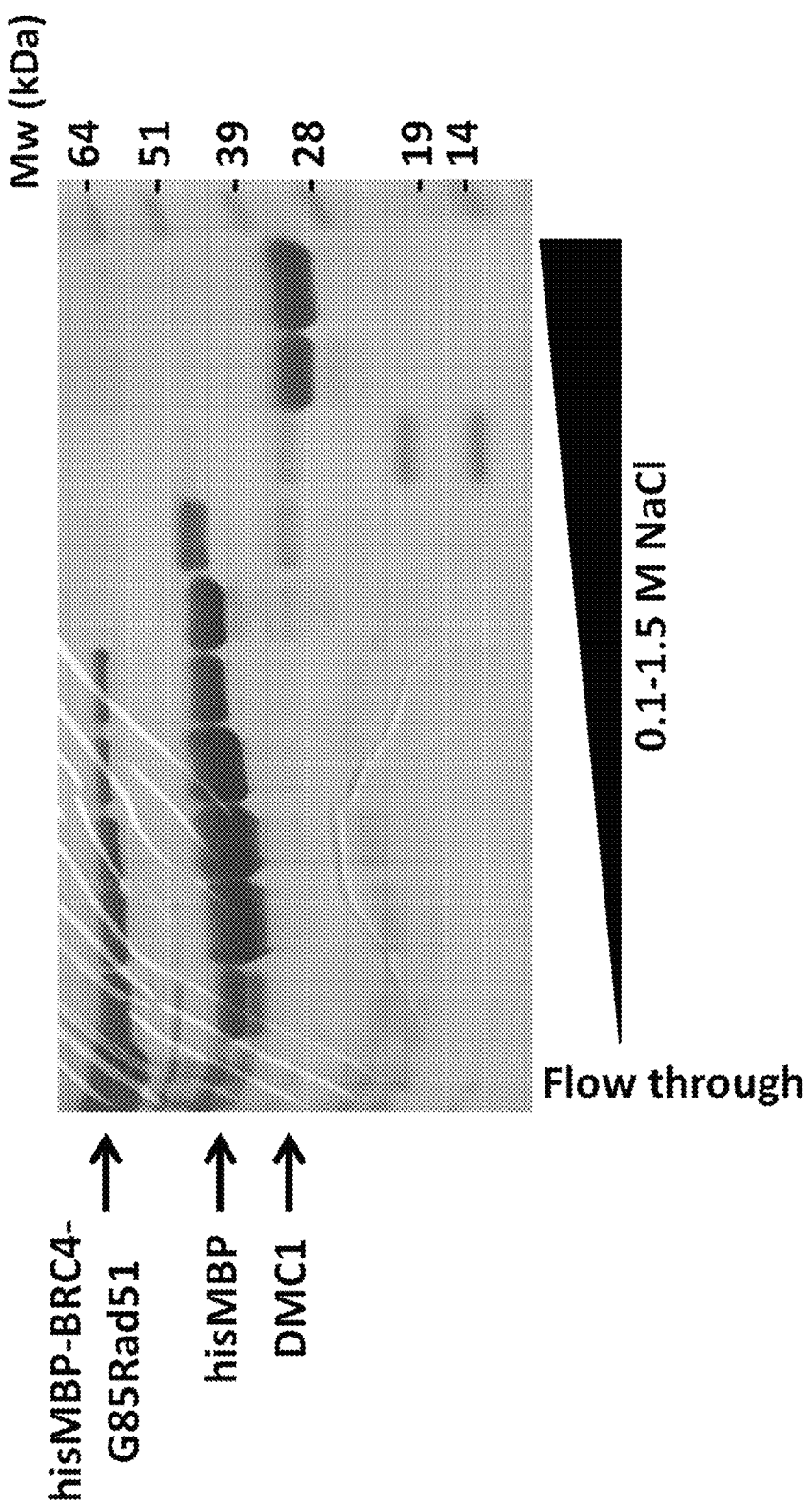
FIG. 14. Coomassie stained SDS-PAGE gel of various elution fractions obtained from DMC1 protein purification via affinity to heparin shown in FIG. 13.
Figure 15:
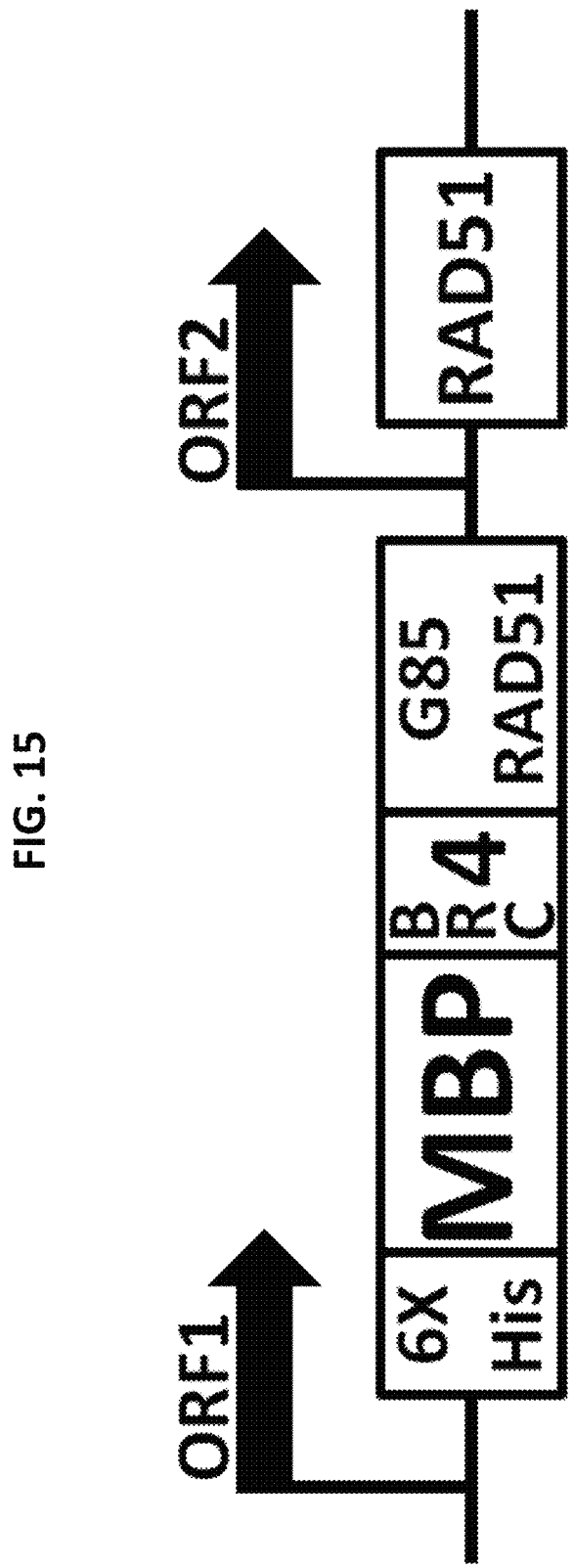
FIG. 15. Diagram representation of vector construct for co-overexpression of 6×his-MBP-tagged-BRC4-Rad51 ATPase domain fusion protein from ORF1 and RAD51 protein from ORF 2.
Figure 16:
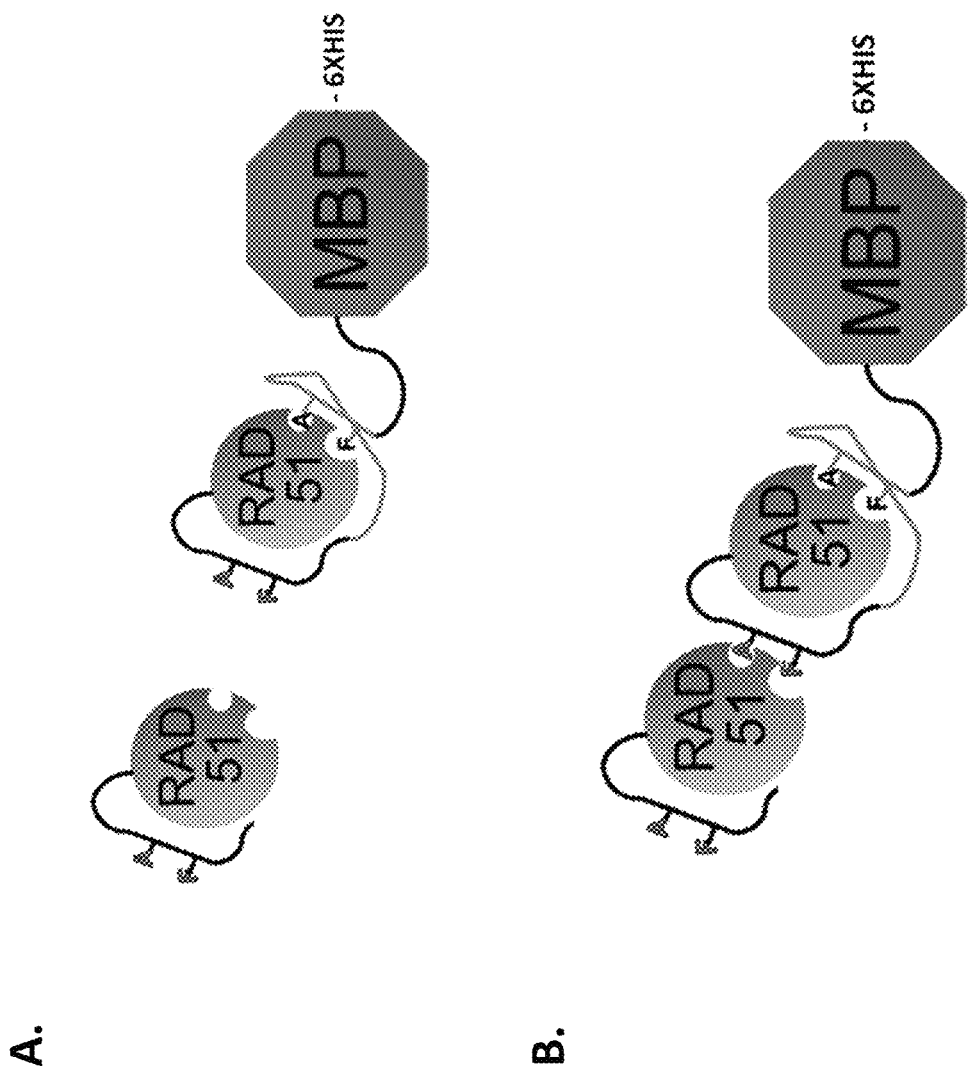
FIG. 16A. Representation of 6×his-MBP-tagged-BRC4-G85RAD51 and RAD51 proteins.
FIG. 16B. Representation of 6×his-MBP-tagged-BRC4-G85RAD51 fusion protein interacting with RAD51 protein.

FIG. 14 is a coomassie stained SDS-PAGE gel of various elution fractions obtained from the heparin affinity chromatography DMC1 purification shown in FIG. 13. FIG. 14 shows that the 6×His-MBP-BRC4-G85RAD1 fusion protein eluted early in the NaCl gradient, whereas the bound DMC1 protein eluted near 600 mM NaCl. Peak fractions containing the DMC1 protein may be pooled together.

The pooled DMC1 protein may be concentrated by any protein concentration means. For example, protein may be concentrated using centrifugal filters units with Molecular Weight Cut Off filters specific to the protein of interest. Protein may be concentrated using any ultrafiltration or depth filtration technique.

The pooled fractions containing the purified DMC1 protein may then be applied onto a size exclusion resin (also known referred to as a gel filtration resin), for example, Superdex 200 resin. The size exclusion resin may be equilibrated with an equilibration buffer, such as 20 mM Tris pH 8.0, 300 mM NaCl prior to injection of the DMC1 sample. Any other size exclusion/gel filtration resin or resin used to separate proteins based on size and or shape may be used.

Any buffer additive such as DTT (for example 1 mM final DTT concentration) may be added to the purified DMC1 sample. The pooled DMC1 protein may be concentrated and snap frozen in liquid $N_2$ for storage in a freezer, for example at −80° C. The pooled DMC1 protein may also be stabilized in a buffer for storage at room temperature, or lyophilized, or prepared for storage in any storage means known by one of ordinary skill in the art.

Purification of DMC1 may be performed in any sequential combination of chromatography resins as described herein as known by one with ordinary skill in the art.

(v) Uses

The present invention may be used to purify recombinase proteins which have an affinity for the RAD51 ATPase F-X-X-A repeat motif or for the BRC4 F-X-X-A repeat motif. The purified recombinase may be used in reagent, diagnostic, and therapeutic applications.

Such use may be employed in, but is not limited to, chromatography, microtiter plates, Western blots, ELISA, or magnetic bead based isolation.

Alternatively, the purified recombinase protein may be used functionally to the action of target molecules. The target molecule may have an activity which the purified recombinase protein enhances or inhibits.

While the specification describes particular embodiments of the present invention, those of ordinary skill in the art can devise variations of the present invention without departing from the inventive concept.

What is claimed is:

1. A method of purifying a recombinase protein, comprising:
    a. inserting at least one expression vector into a single host cell, wherein said at least one expression vector comprises at least a first coding sequence and a second coding sequence, and the first coding sequence and the second coding sequence is under the control of at least one promoter, wherein the first coding sequence encodes for a tagged fusion protein comprising a BRCA2 protein motif comprising at least one BRC repeat comprising an F-X-X-A motif as shown in the amino acid sequence 409-412 in SEQ ID NO: 22, and the second coding sequence encodes for a recombinase protein that has a binding affinity to the BRCA2 protein motif of the first coding sequence;
    b. expressing the tagged fusion protein and the recombinase protein from under the control of the at least one promoter in the host cell; and
    c. isolating the recombinase protein from the host cell using a protein purification procedure that comprises of procedures that select for the tagged fusion protein.

2. The method of claim 1, wherein the tagged fusion protein comprises at least one protein tag.

3. The method of claim 2 wherein said at least one protein tag comprises a 6×his tag, an MBP tag, a GST tag, a FLAG tag, a myc tag, or a Strep tag or any combination of protein tags.

4. The method of claim 2, wherein the first coding sequence further comprises a 6×his tag and an MBP tag and the BRC4 protein motif, wherein the first coding sequence codes for a protein as set forth in SEQ ID NO: 22.

5. The method of claim 1, wherein the second coding sequence encodes for human RAD51 recombinase.

6. The method of claim 1 wherein the protein purification procedure comprises a first ligand that binds to the tagged fusion protein and because the recombinase is bound to the tagged fusion protein, the first ligand is used to isolate both the tagged fusion protein and the recombinase protein together.

7. The method of claim 6 wherein the tagged fusion protein and the recombinase protein are separated from each other using a second ligand, wherein the second ligand has a competing affinity for the recombinase protein with the tagged fusion protein.

8. The method of claim 7 wherein the recombinase protein is further purified using a method that selects proteins based on their size.

9. The method of claim 6 wherein the first ligand comprises a metal chelator and/or amylase ligand.

10. The method of claim 7 wherein the second ligand is heparin.

* * * * *

UNITED STATES PATENT AND TRADEMARK OFFICE
CERTIFICATE OF CORRECTION

PATENT NO. : 10,604,778 B2
APPLICATION NO. : 15/555966
DATED : March 31, 2020
INVENTOR(S) : Michael Longo Page 1 of 1

It is certified that error appears in the above-identified patent and that said Letters Patent is hereby corrected as shown below:

On the Title Page

Item (54) and in the Specification Column 1 Lines 1-2 Title of the invention is incorrectly stated as follows: "BRCA2 MEDIATED PROTEIN PURIFICATION RECOMBINASE". The correct and full Title is: "BRCA2 MEDIATED PROTEIN PURIFICATION OF RECOMBINASE".

Signed and Sealed this
Nineteenth Day of October, 2021

Drew Hirshfeld
*Performing the Functions and Duties of the*
*Under Secretary of Commerce for Intellectual Property and*
*Director of the United States Patent and Trademark Office*